United States Patent
Wise et al.

(10) Patent No.: US 12,064,116 B2
(45) Date of Patent: Aug. 20, 2024

(54) CIRCULAR SURGICAL STAPLER WITH ANASTOMOSIS RELEASE FEATURE

(71) Applicant: Cilag GmbH International, Zug (CH)

(72) Inventors: Austin E. Wise, Cincinnati, OH (US); Shane R. Adams, Lebanon, OH (US)

(73) Assignee: Cilag GmbH International, Zug (CH)

( * ) Notice: Subject to any disclaimer, the term of this patent is extended or adjusted under 35 U.S.C. 154(b) by 141 days.

(21) Appl. No.: 17/489,871

(22) Filed: Sep. 30, 2021

(65) Prior Publication Data
US 2023/0102965 A1 Mar. 30, 2023

(51) Int. Cl.
*A61B 17/115* (2006.01)
*A61B 17/00* (2006.01)
*A61B 17/072* (2006.01)
*A61B 90/00* (2016.01)

(52) U.S. Cl.
CPC . *A61B 17/1155* (2013.01); *A61B 2017/00398* (2013.01); *A61B 2017/07264* (2013.01); *A61B 2017/07285* (2013.01); *A61B 2090/061* (2016.02)

(58) Field of Classification Search
CPC ...... A61B 17/1155; A61B 2017/00398; A61B 2017/07264; A61B 2017/07285; A61B 2090/061
USPC .................................... 227/175.1–182.1, 120
See application file for complete search history.

(56) References Cited

U.S. PATENT DOCUMENTS

| | | | | |
|---|---|---|---|---|
| 4,198,982 A | * | 4/1980 | Fortner | A61B 17/115 227/19 |
| 4,556,058 A | * | 12/1985 | Green | A61B 17/128 606/174 |
| 4,903,697 A | * | 2/1990 | Resnick | A61B 17/115 227/19 |
| 5,222,963 A | * | 6/1993 | Brinkerhoff | A61B 17/11 411/509 |
| 5,271,543 A | | 12/1993 | Grant et al. | |

(Continued)

FOREIGN PATENT DOCUMENTS

| | | |
|---|---|---|
| CN | 106667537 A | 5/2017 |
| EP | 1550414 A2 | 7/2005 |

OTHER PUBLICATIONS

International Search Report and Written Opinion dated Dec. 22, 2022 for Application No. PCT/IB2022/059171, 13 pgs.

*Primary Examiner* — Robert F Long
(74) *Attorney, Agent, or Firm* — Frost Brown Todd LLP

(57) ABSTRACT

A surgical stapling instrument includes an anvil defining a plurality of staple forming pockets, and a stapling head assembly, and a retracting assembly. The stapling head assembly includes a body, a coupling member capable of actuating the anvil, a deck surface, a staple driver assembly, and a knife member. The staple driver assembly actuates through a first firing stroke and a second firing stroke. In the first firing stroke, the staple driver assembly drives a plurality of staples against the staple forming pockets. In the second firing stroke, the staple driver actuates distally past the deck surface. The knife member includes a cutting edge that can sever tissue during the first firing stroke while remaining in a retracted position that is proximal relative to the staple deck surface during the second firing stroke. The retracting assembly can drive the knife member into the retracted position during the first firing stroke.

18 Claims, 29 Drawing Sheets

(56) References Cited

U.S. PATENT DOCUMENTS

| | | | |
|---|---|---|---|
| 5,292,053 A | 3/1994 | Bilotti et al. | |
| 5,333,773 A | 8/1994 | Main et al. | |
| 5,350,104 A | 9/1994 | Main et al. | |
| 5,533,661 A | 7/1996 | Main et al. | |
| 8,267,301 B2* | 9/2012 | Milliman | A61B 17/115 227/176.1 |
| 8,439,246 B1* | 5/2013 | Knodel | A61B 90/92 227/176.1 |
| 8,910,847 B2 | 12/2014 | Nalagatla et al. | |
| 9,351,724 B2* | 5/2016 | Penna | A61B 17/068 |
| 9,504,470 B2* | 11/2016 | Milliman | A61B 17/07292 |
| 9,572,572 B2* | 2/2017 | Williams | A61B 17/1155 |
| 9,713,469 B2 | 7/2017 | Leimbach et al. | |
| 9,730,694 B2* | 8/2017 | Scirica | A61B 17/1155 |
| 9,750,503 B2* | 9/2017 | Milliman | A61B 90/98 |
| 9,814,463 B2* | 11/2017 | Williams | A61B 17/07207 |
| 9,907,552 B2 | 3/2018 | Measamer et al. | |
| 9,936,949 B2 | 4/2018 | Measamer et al. | |
| 10,136,888 B2* | 11/2018 | Chen | A61B 17/1155 |
| 10,542,993 B2* | 1/2020 | Guerrera | A61B 17/07207 |
| 10,631,866 B2 | 4/2020 | Laurent et al. | |
| 10,667,818 B2 | 6/2020 | McClain et al. | |
| 10,687,819 B2 | 6/2020 | Stokes et al. | |
| 10,709,452 B2 | 7/2020 | DiNardo et al. | |
| 10,874,398 B2 | 12/2020 | Baxter, III et al. | |
| 10,898,187 B2 | 1/2021 | Deck et al. | |
| 10,905,419 B2 | 2/2021 | Schings et al. | |
| 10,932,781 B2 | 3/2021 | Jones et al. | |
| 11,033,266 B2 | 6/2021 | Jones et al. | |
| 11,045,193 B2 | 6/2021 | Schings et al. | |
| 2011/0290854 A1* | 12/2011 | Timm | A61B 17/068 227/178.1 |
| 2012/0074201 A1* | 3/2012 | Baxter, III | A61B 17/07207 606/1 |
| 2013/0274771 A1* | 10/2013 | Williams | A61B 17/072 606/153 |
| 2014/0183244 A1* | 7/2014 | Duque | A61B 17/068 606/167 |
| 2015/0083772 A1 | 3/2015 | Miller et al. | |
| 2016/0007999 A1* | 1/2016 | Latimer | A61B 17/1155 227/177.1 |
| 2018/0125495 A1* | 5/2018 | Sgroi, Jr. | A61B 17/07207 |
| 2018/0132849 A1 | 5/2018 | Miller et al. | |
| 2019/0015105 A1* | 1/2019 | Milliman | A61B 17/1155 |
| 2019/0282233 A1* | 9/2019 | Burbank | A61B 17/07207 |
| 2020/0046353 A1 | 2/2020 | Deck et al. | |
| 2020/0276693 A1* | 9/2020 | Sgroi, Jr. | B25C 5/1617 |
| 2021/0038223 A1 | 2/2021 | Schings et al. | |
| 2023/0102965 A1* | 3/2023 | Wise | A61B 17/1155 227/175.1 |

\* cited by examiner

CIRCULAR SURGICAL STAPLER WITH ANASTOMOSIS RELEASE FEATURE

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
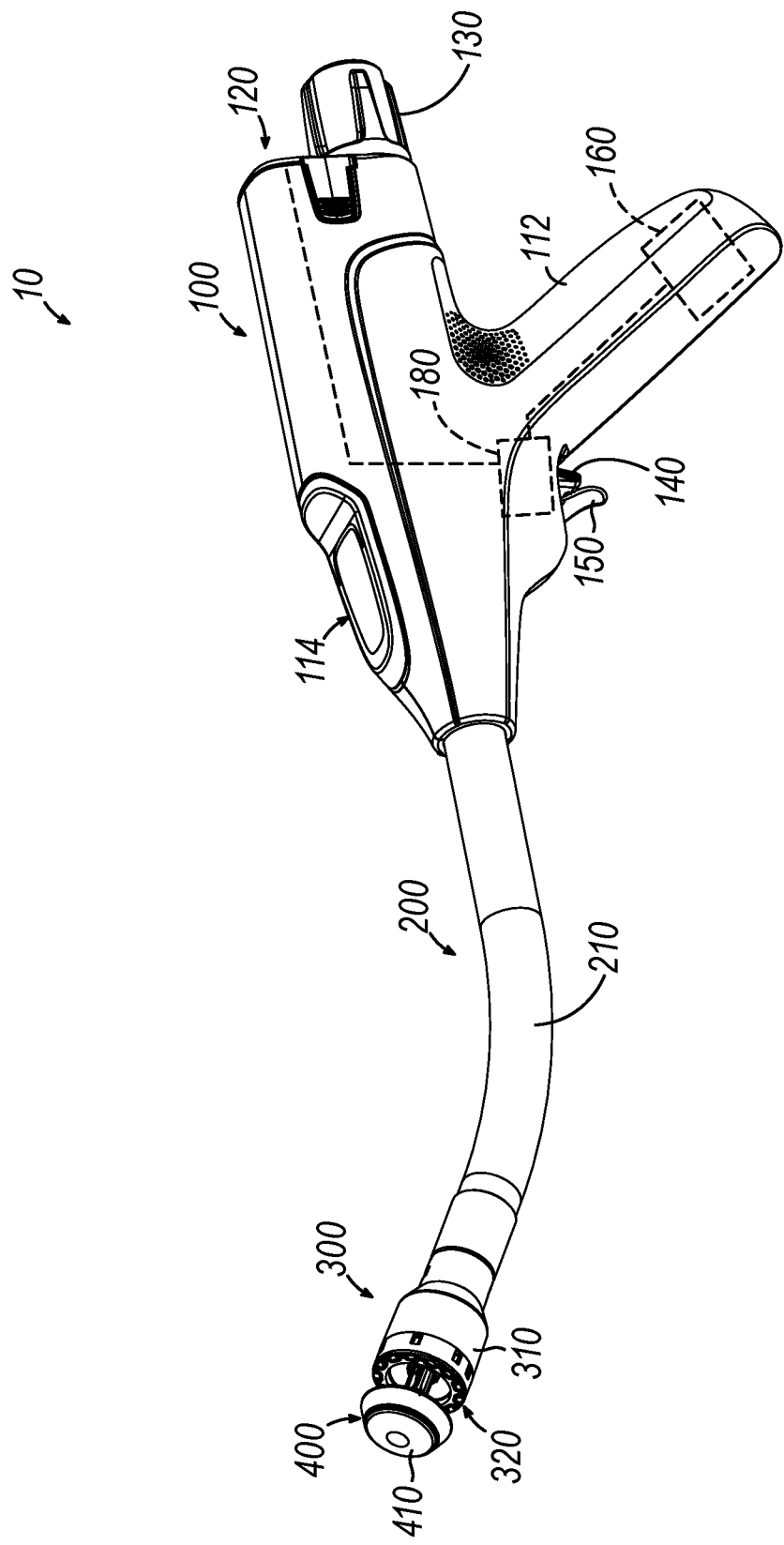
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings.

The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
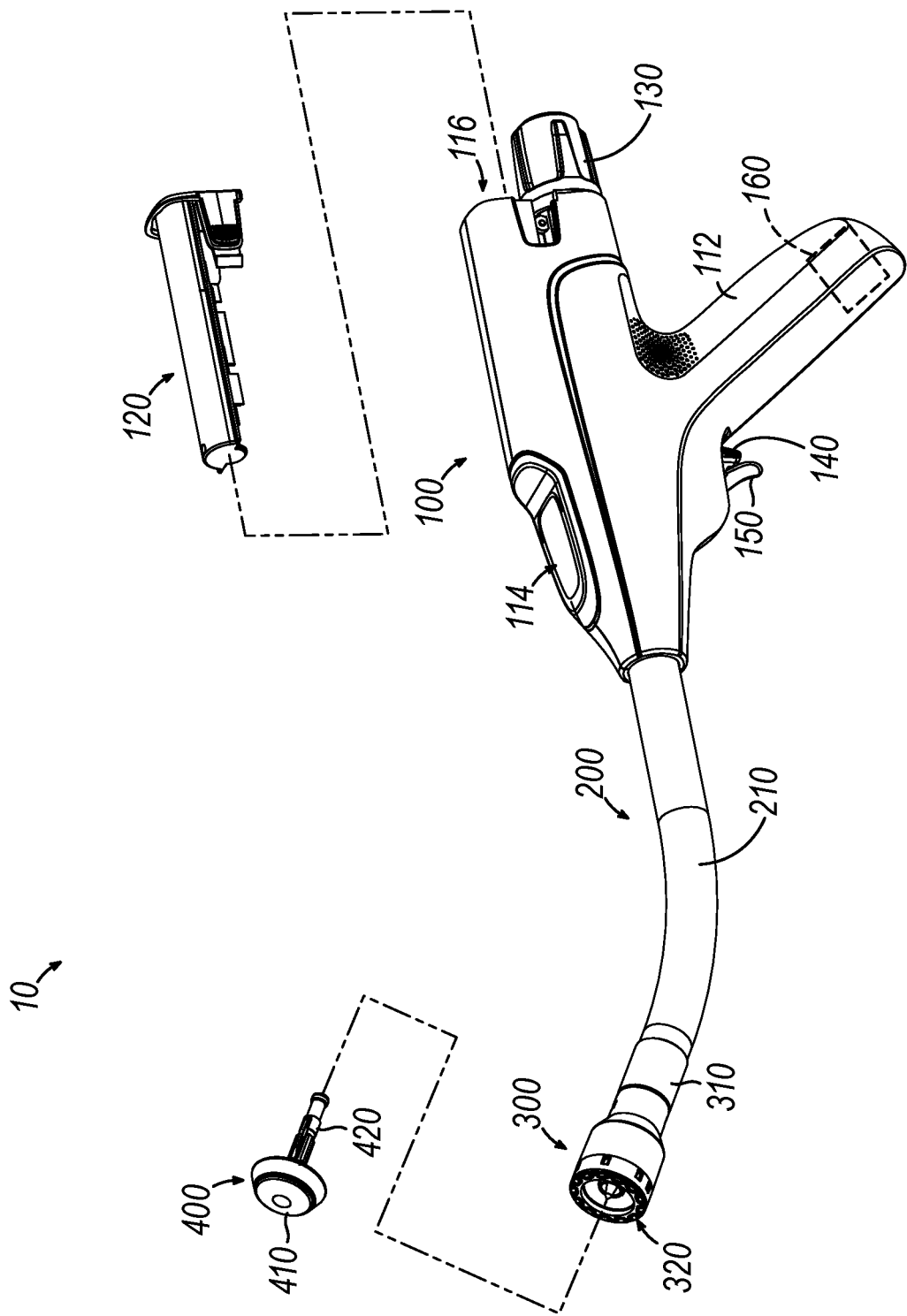
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
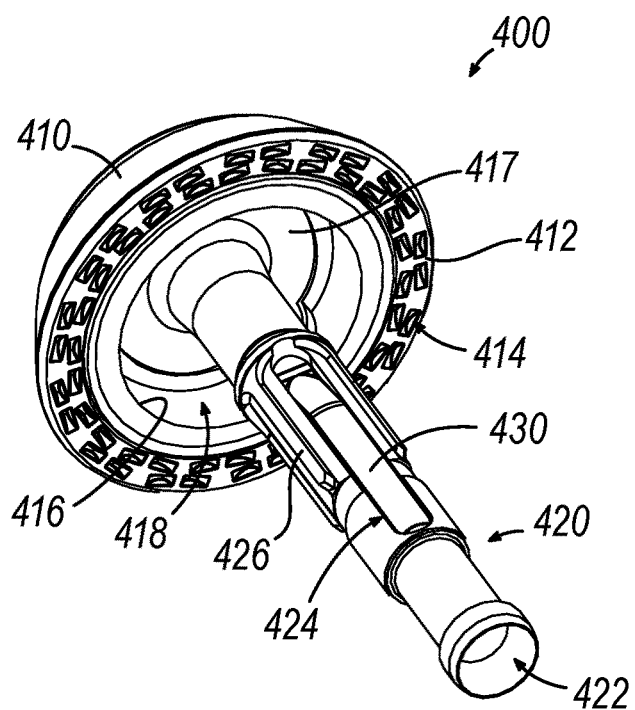
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
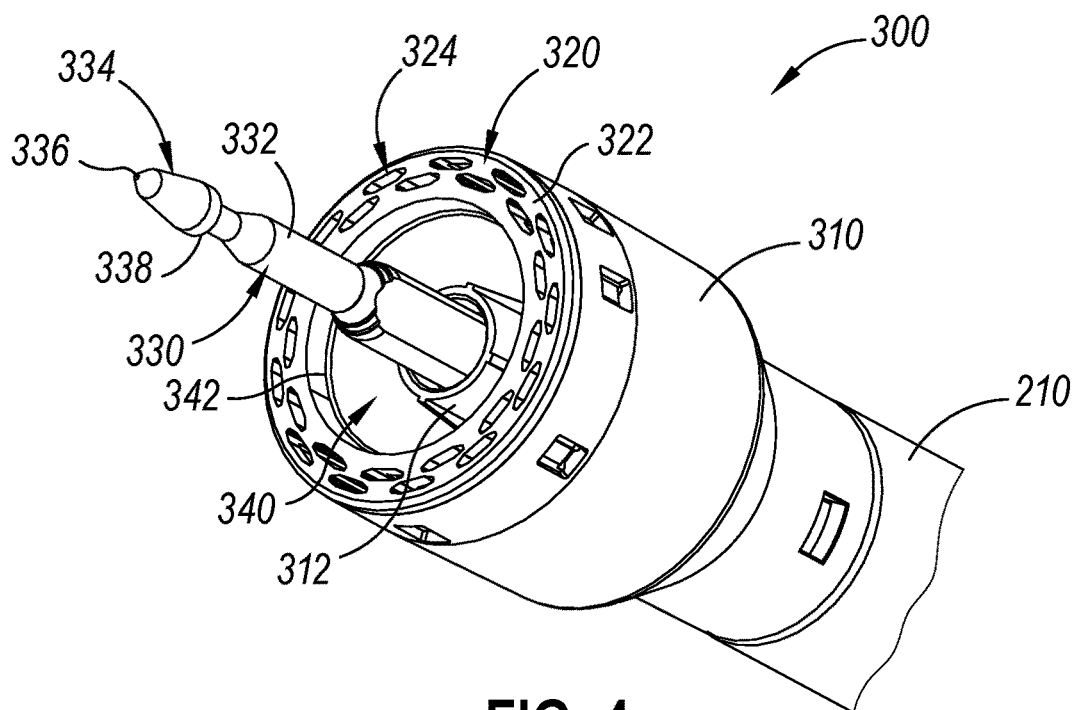
FIG. 4 depicts a perspective view of the stapling head assembly of the circular stapler of FIG. 1.
Figure 5:
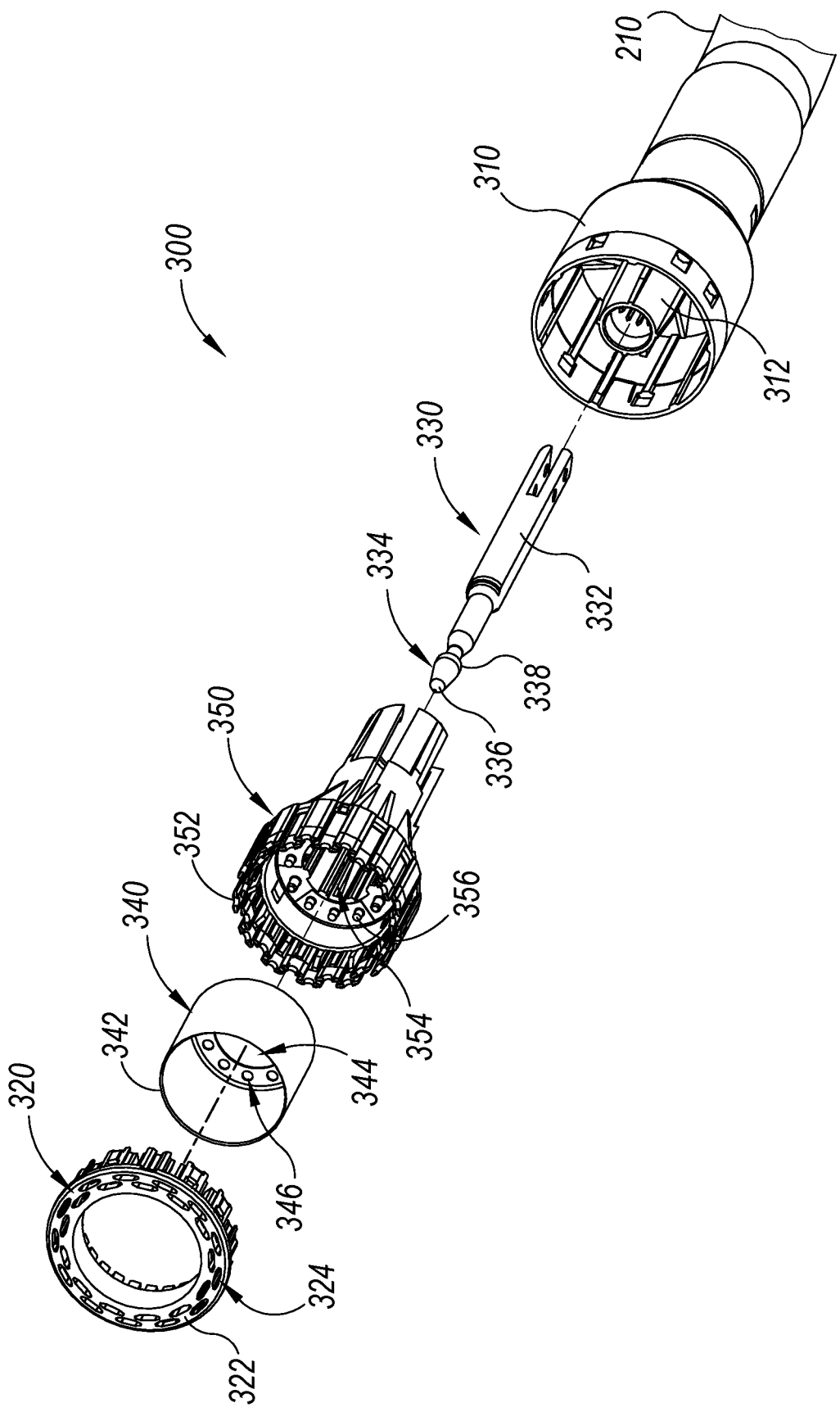
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening (344) that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

Figure 9:
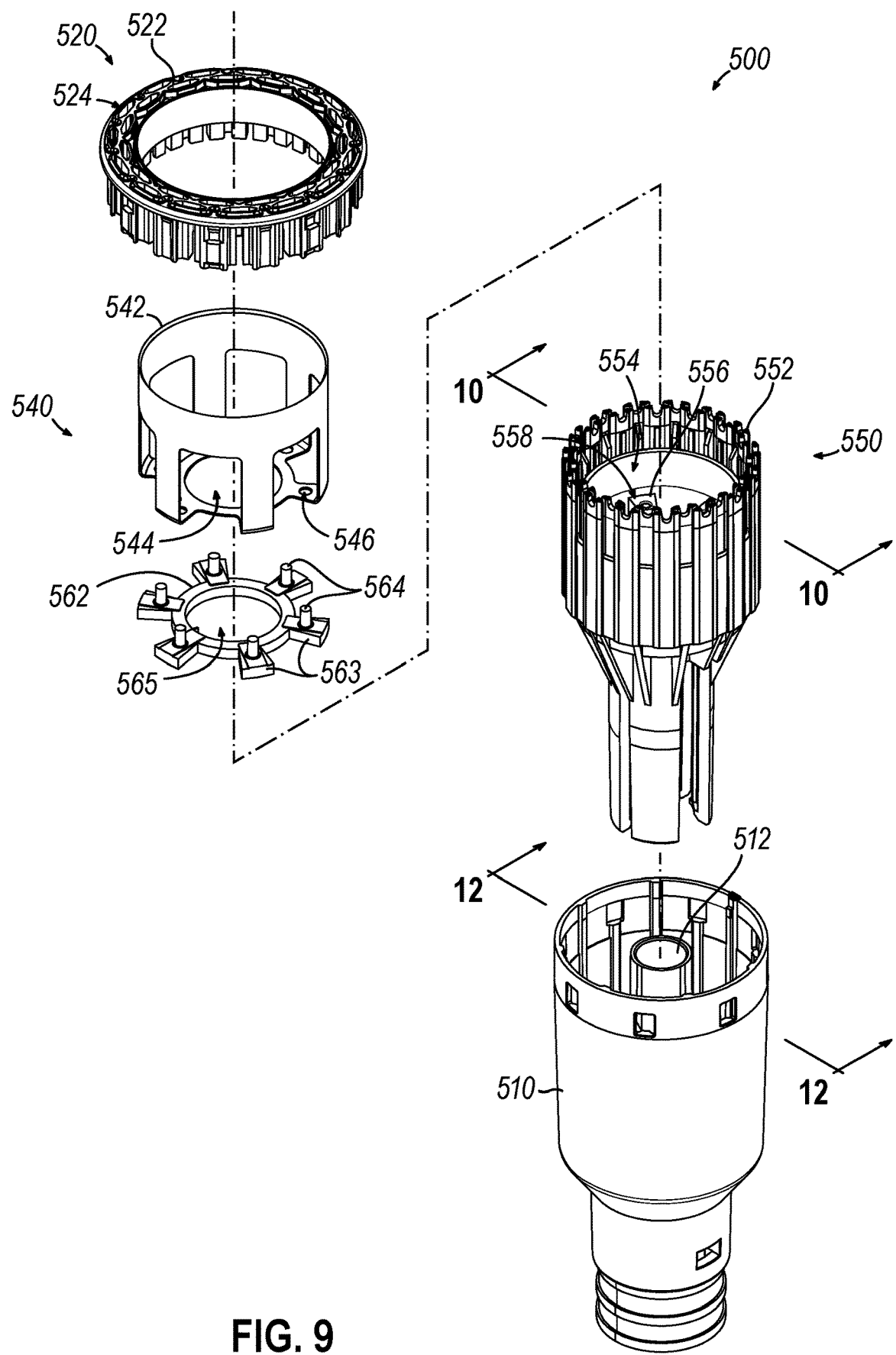
FIG. 9 depicts an exploded perspective view of the stapling head assembly of FIG. 8.

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 9, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
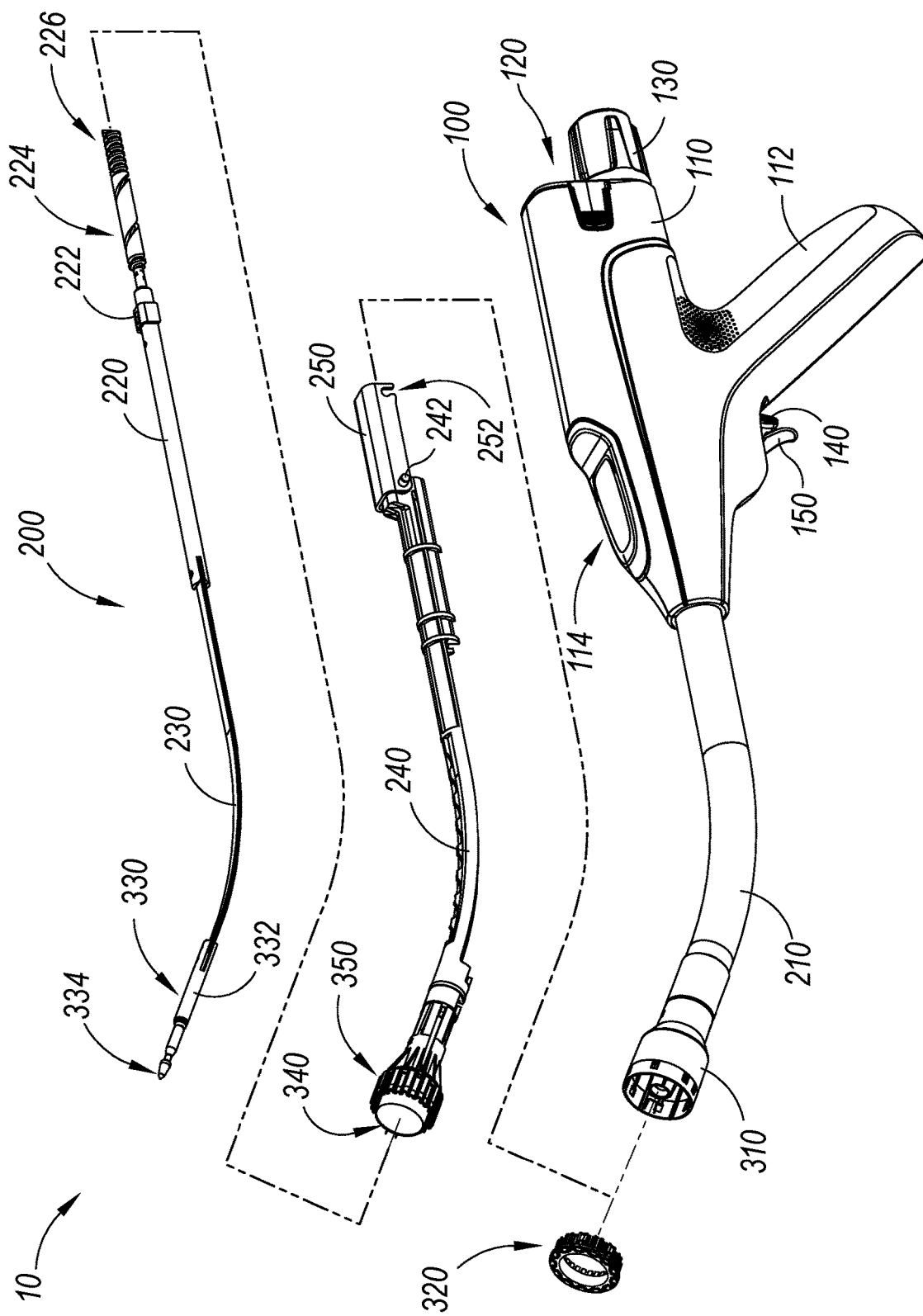
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7F show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
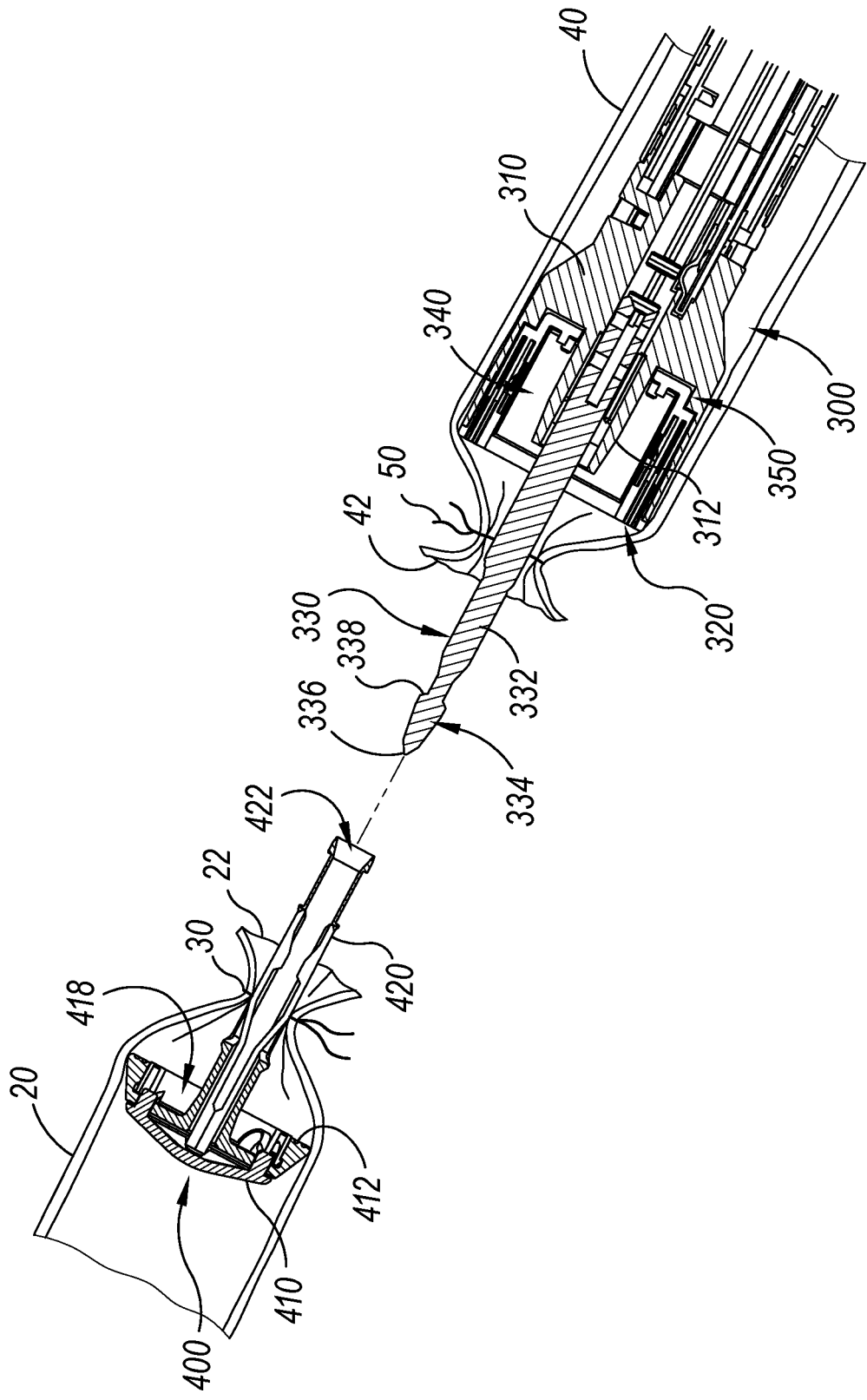
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
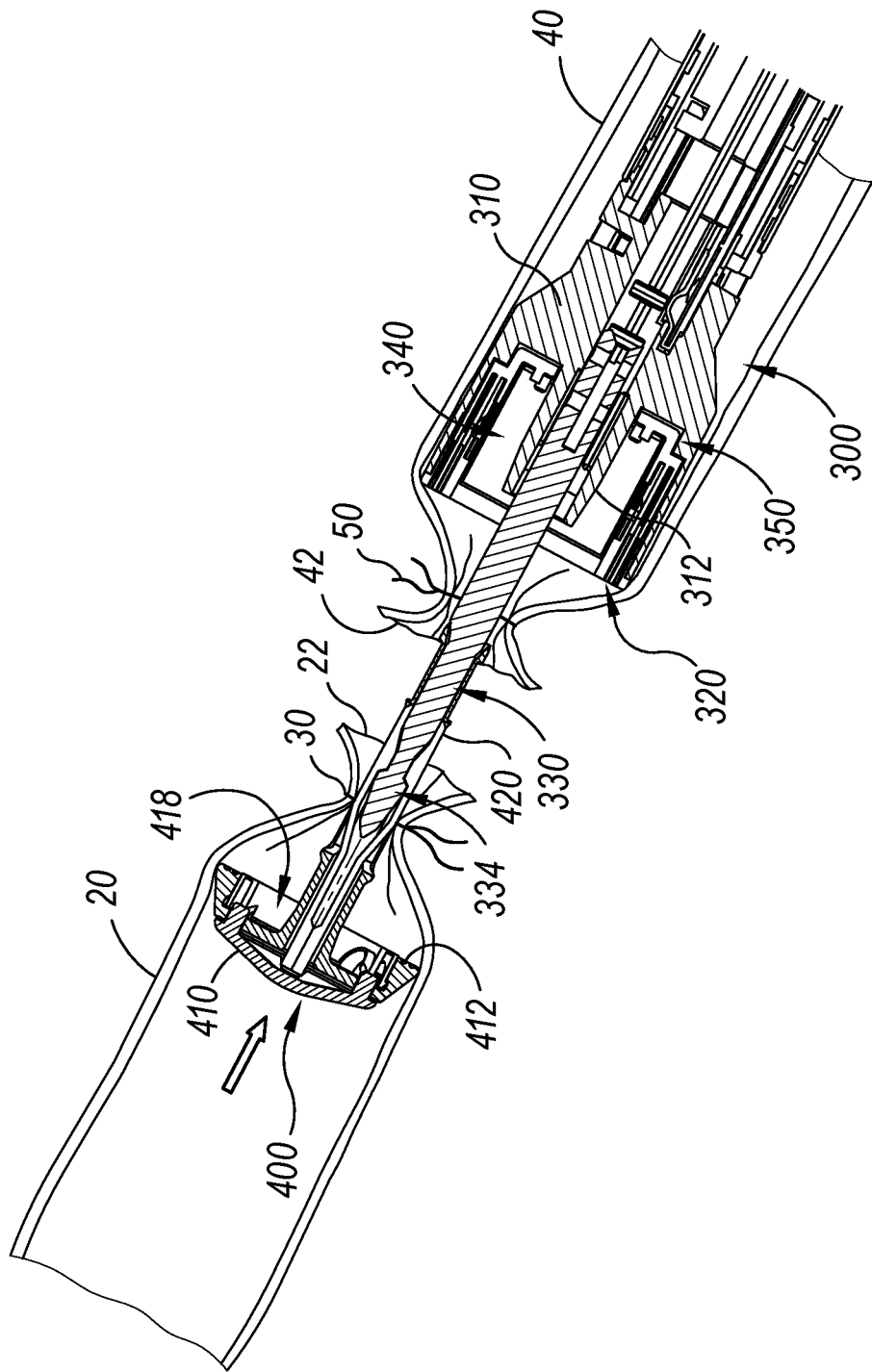
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
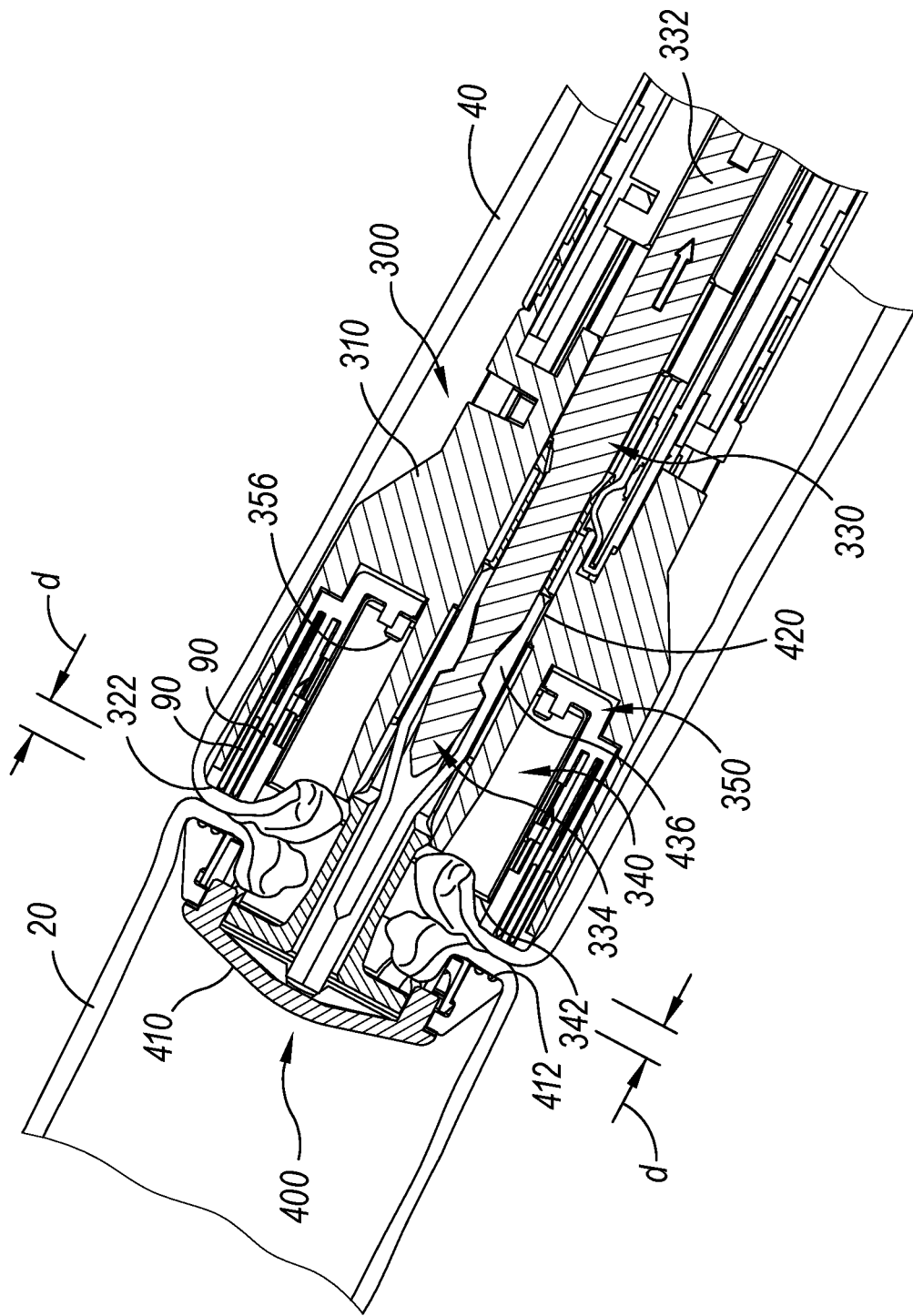
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
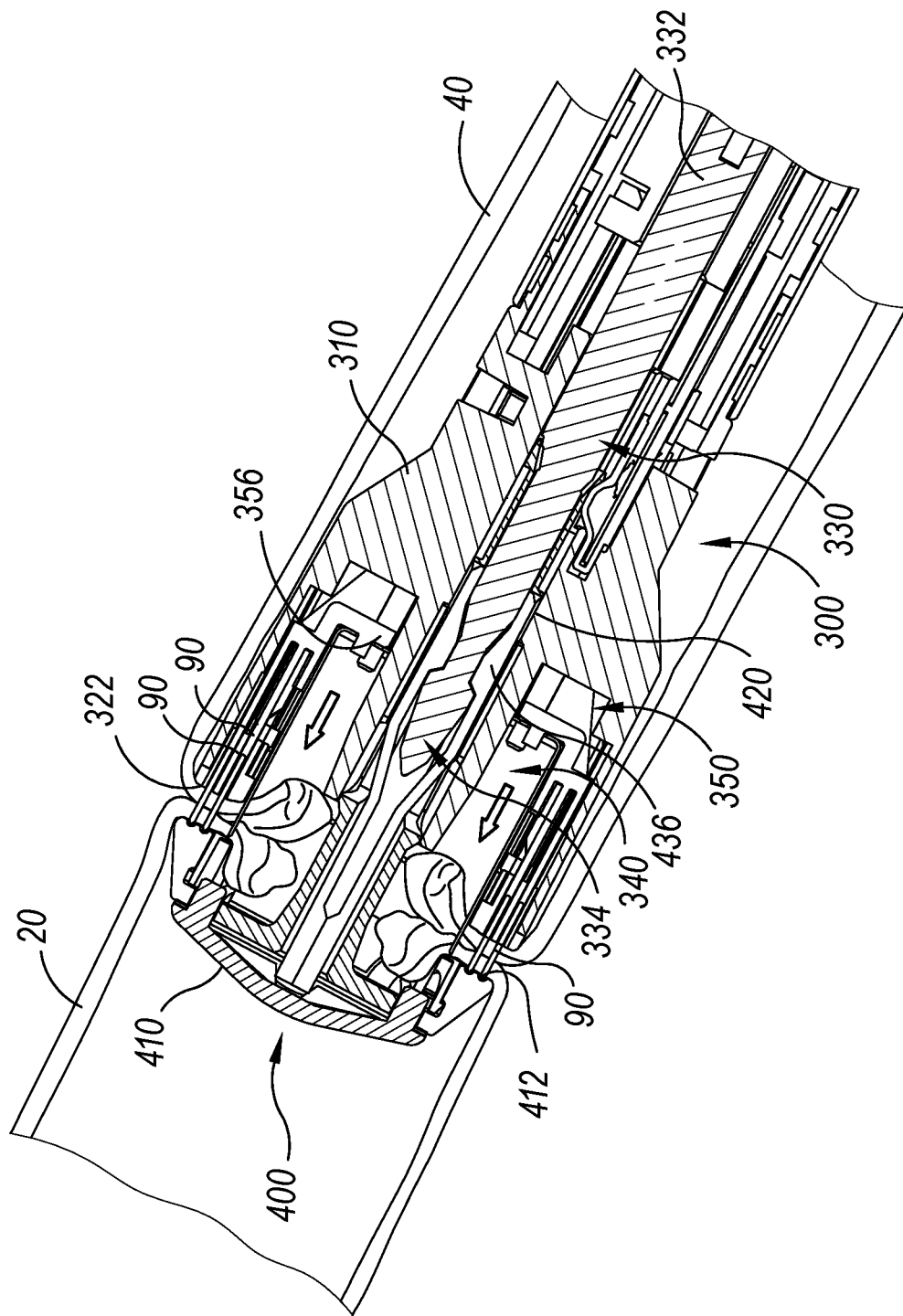
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
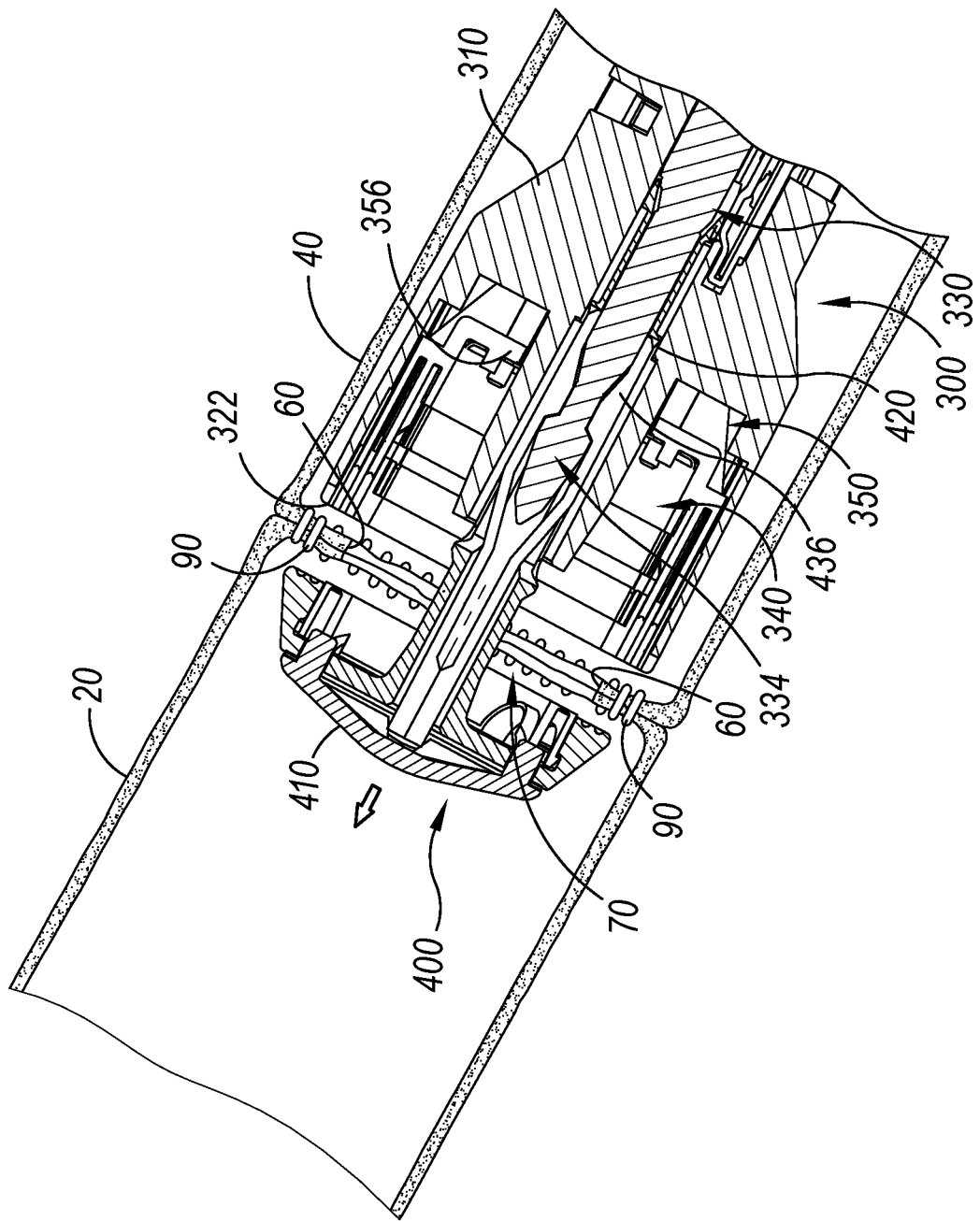
FIG. 7E depicts a cross-sectional side view of the anvil of FIG. 3 positioned within the first section of the digestive tract and the stapling head assembly of FIG. 4 positioned within the second section of the digestive tract, with an end-to-end anastomosis formed and the anvil actuated distally from the stapling head assembly to release the previously clamped tissue between the anvil and the stapling head assembly.
Figure 7F:
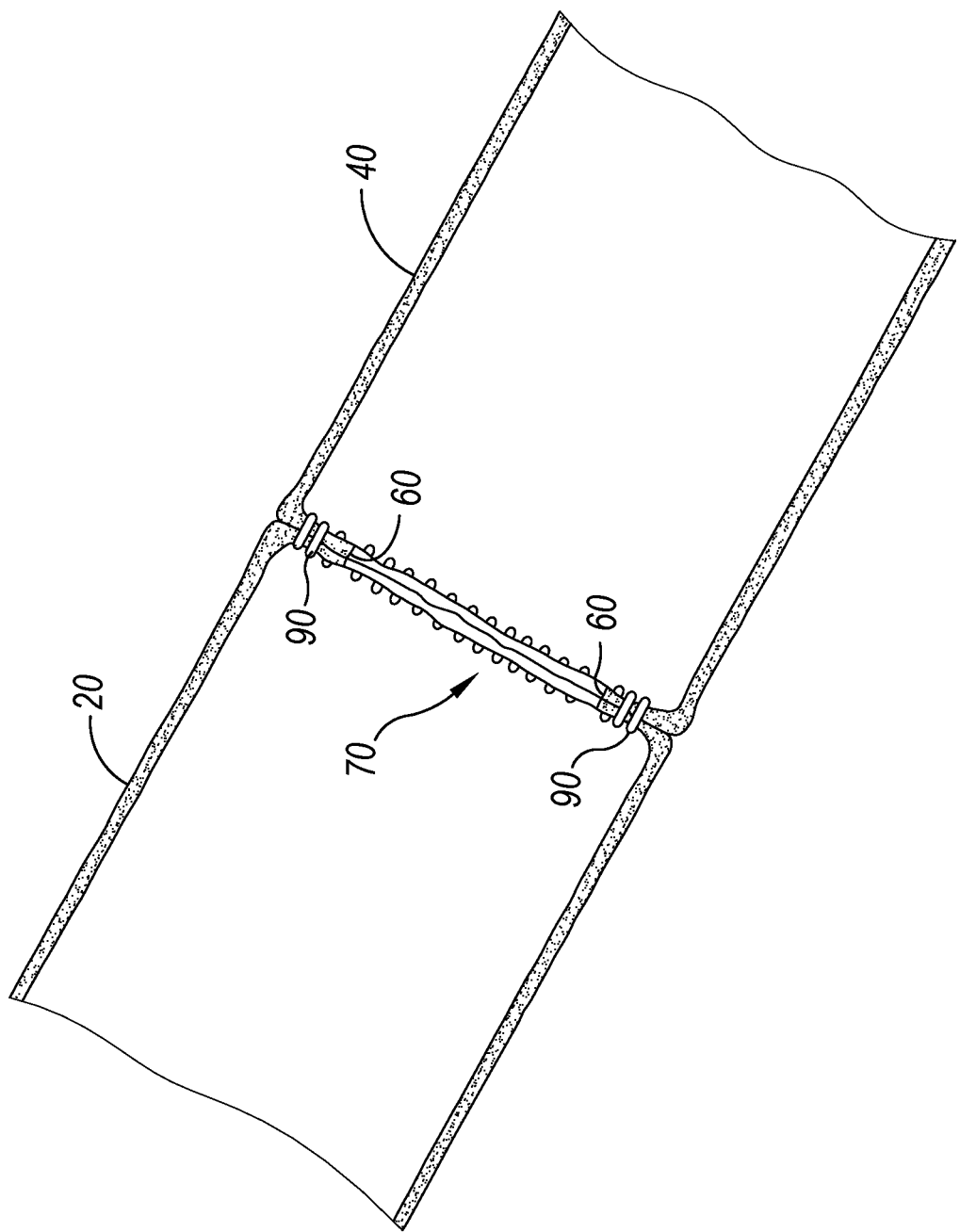
FIG. 7F depicts a cross-sectional side view of the first and second sections of the digestive tract of FIG. 7A joined together at an end-to-end anastomosis formed with the circular stapler of FIG. 1.
Figure 8:
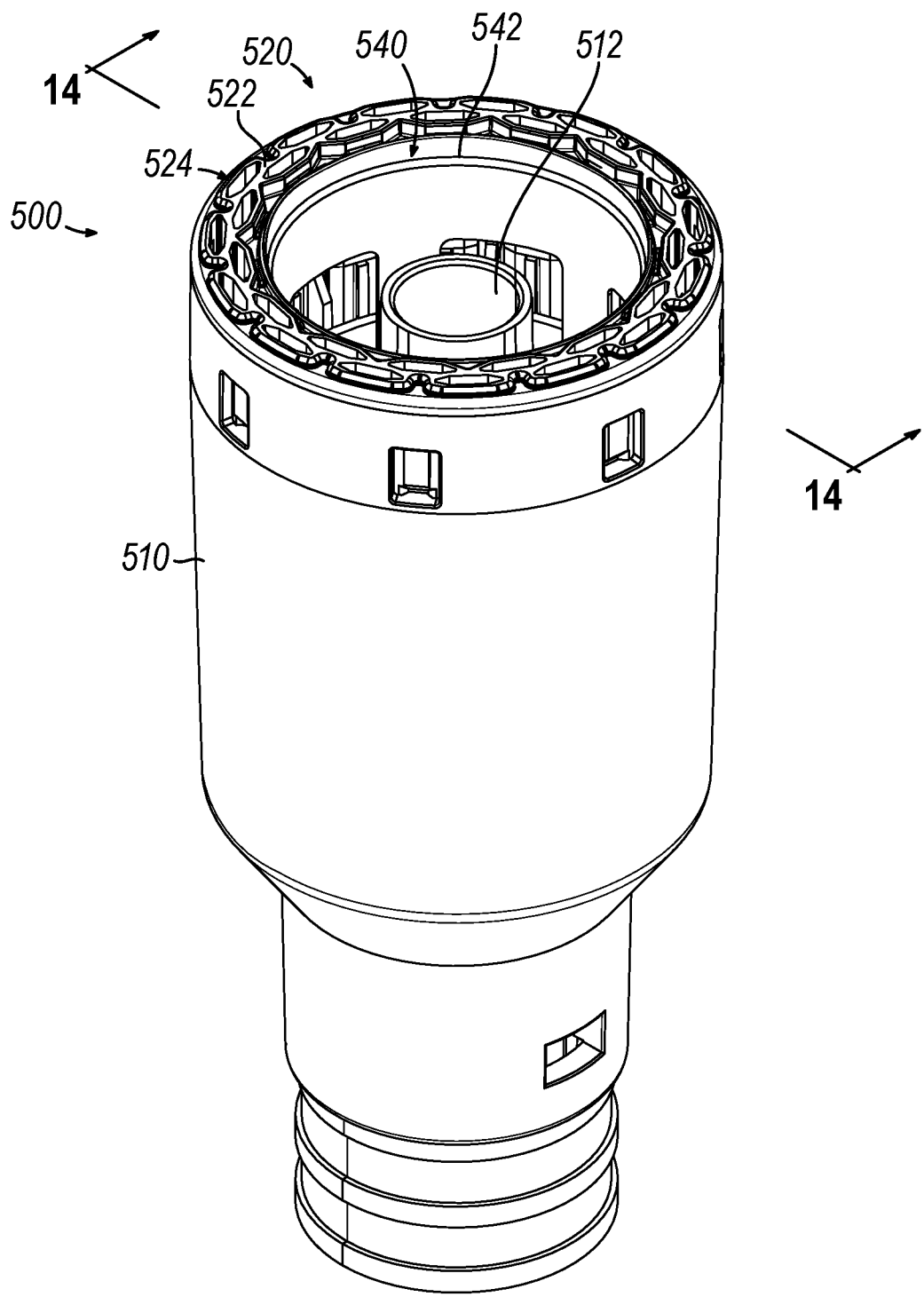
FIG. 8 depicts a perspective view of an alternative stapling head assembly that may be readily incorporated into the circular surgical stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322) as shown in FIG. 7E. The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7F. The inner diameter of the anastomosis (70) is defined by the severed edge (60) left by knife member (340).

II. Exemplary Circular Stapling Instrument with Anastomosis Release Features

As mentioned above, after the operator has actuated stapling head assembly (300) in order to sever and staple tissue in accordance with the description herein, the operator may drive anvil (400) distally away from stapling head assembly (300) to thereby increase the gap distance (d) and facilitate the release of tissue between surfaces (412, 322). However, in some instances, tissue that was previously clamped by anvil (400) and stapling head assembly (300) may become undesirably associated with (i.e., adhere to, cling to, etc.) surface (322) of stapling head assembly (300) such that after gap distance (d) is increased, the tissue of the newly formed anastomosis adheres to, clings, to, and/or sticks with surface (322) thereby inhibiting a desirable release of tissue. Therefore, in some instances, it may be desirable to incorporate an anastomosis release feature that pushes the tissue of the newly formed anastomosis off surface (322) in order to further promote release of such tissue from surface (322).

FIGS. 8-13H and 14A-14D show various features of an alternative stapling head assembly (500) that may readily incorporated into instrument (10) in replacement of stapling head assembly (300). Stapling head assembly (500) is substantially similar to stapling head assembly (300) described above, with differences elaborated below. In particular, stapling head assembly (500) includes a knife retracting assembly (560) (see FIGS. 14A-14D) configured to proximally retract a cylindraceous knife member (540) within a bore (554) defined by staple drivers (552) after the initial firing of stapling head assembly (500); thereby rendering cylindraceous knife member (540) inoperable such that staple drivers (552) may be actuated distally past staple surface (522) a second time in order to push tissue off staple surface (522) while knife member (540) remains proximally housed relative to staple surface (522). Therefore, staple drivers (522) may act as an anastomosis release feature after performing the staple driving function in accordance with the description herein.

Turning to FIG. 9, stapling head assembly (500) includes a tubular body member (510), an inner core member (512), an annular deck member (520), a deck surface (522) defining a plurality of staple openings (524), a trocar (530) (see FIGS. 13A-13H), a cylindraceous knife member (540) defining a central opening (544) and an annular array of openings (566), a sharp circular cutting edge (542), staple driver member (550), and a plurality of staple drivers (552); which may be substantially similar to tubular body member (310), inner core member (312), annular deck member (320), deck surface (322), staple openings (324), trocar (330), cylindraceous knife member (340), central opening (344), annular array of openings (366), cutting edge (342), staple driver member (350), and plurality of staple drivers (352) described above, respectively, with differences elaborated below.

Figure 10:
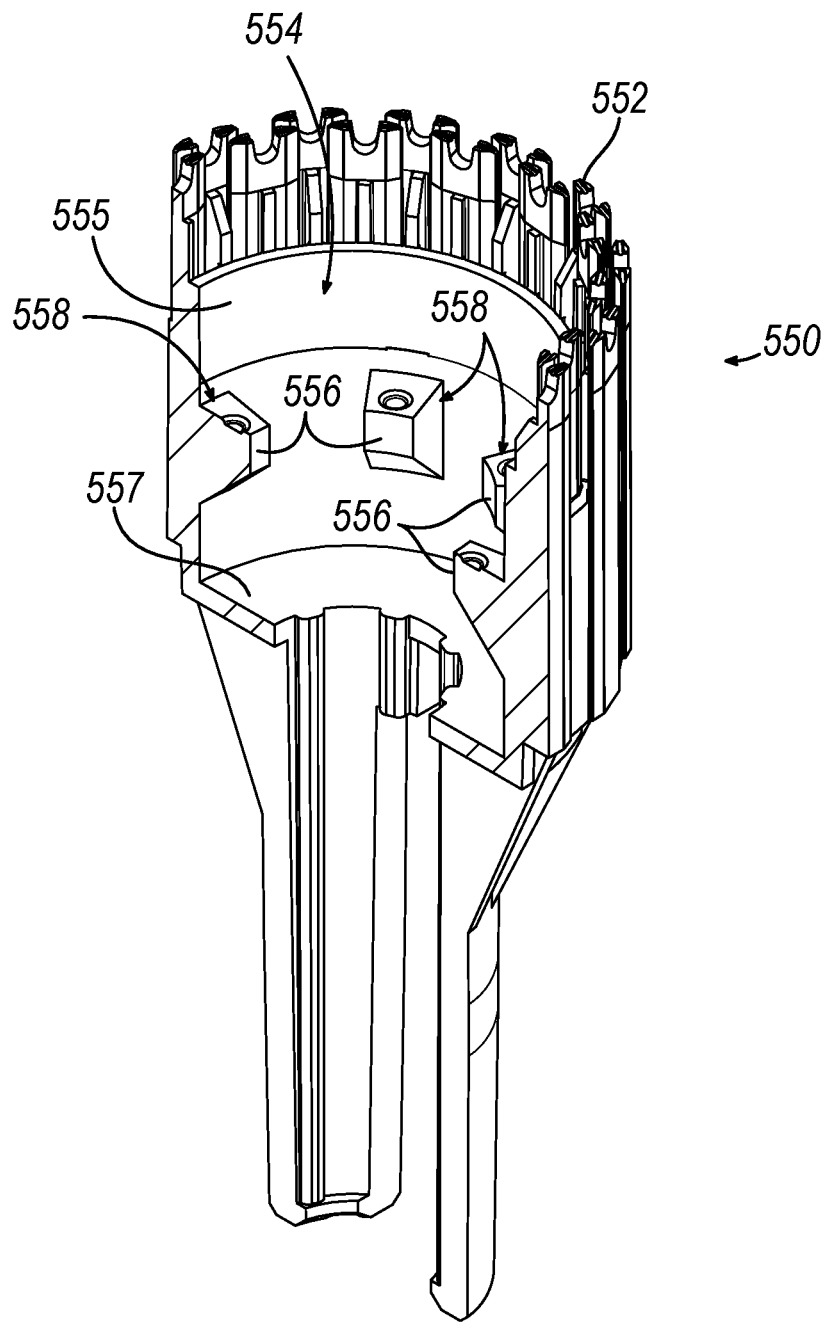
FIG. 10 depicts a sectional view of a staple driver member of the stapling head assembly of FIG. 8, taken along line 10-10 of FIG. 9.

Similar to staple driver member (350) described above, staple driver member (550) is configured to actuate relative to tubular body member (510) in order to drive a plurality of staples through staple openings (524) and against anvil (400). As best seen in FIG. 10, rather than having a plurality of studs (356) located at a floor of stapler driver member (350) configured to fixedly couple with knife member (340) via annular array of openings (346), staple driver member (550) of the current example includes an annular array of firing ledges (556) extending radially inward from an interior annular surface (555). In the current example, firing ledges (556) each define a respective recessed pocket (558) dimensioned to selectively house a respective locating bump (566) (see FIG. 11) of a knife coupling ring (562) (see FIG. 11). Firing ledges (556) are located distally from a floor surface (557) of stapler driver member (350).

Firing ledges (556) are attached to interior annular surface (555) such that firing ledges (556) are configured to actuate with the rest of staple driver member (550) in accordance with the description herein. Firing ledges (556) are configured to engage a respective ledge engagement body (563) (see FIG. 11) of a knife coupling ring (562) such that distal actuation of firing ledges (556) drives distal actuation of knife coupling ring (562) and knife (540) during the stapling and severing of tissue in accordance with the description herein. As will be described in greater detail below, knife retracting assembly (560) (see FIGS. 13A-13H) is configured to actuate knife coupling ring (562) out of engagement with firing ledges (556) and toward floor surface (557) as knife coupling ring (562) and knife (540) are further driven distally by firing ledge (556) after or during the completion of the stapling/severing process in accordance with the description herein.

Figure 11:
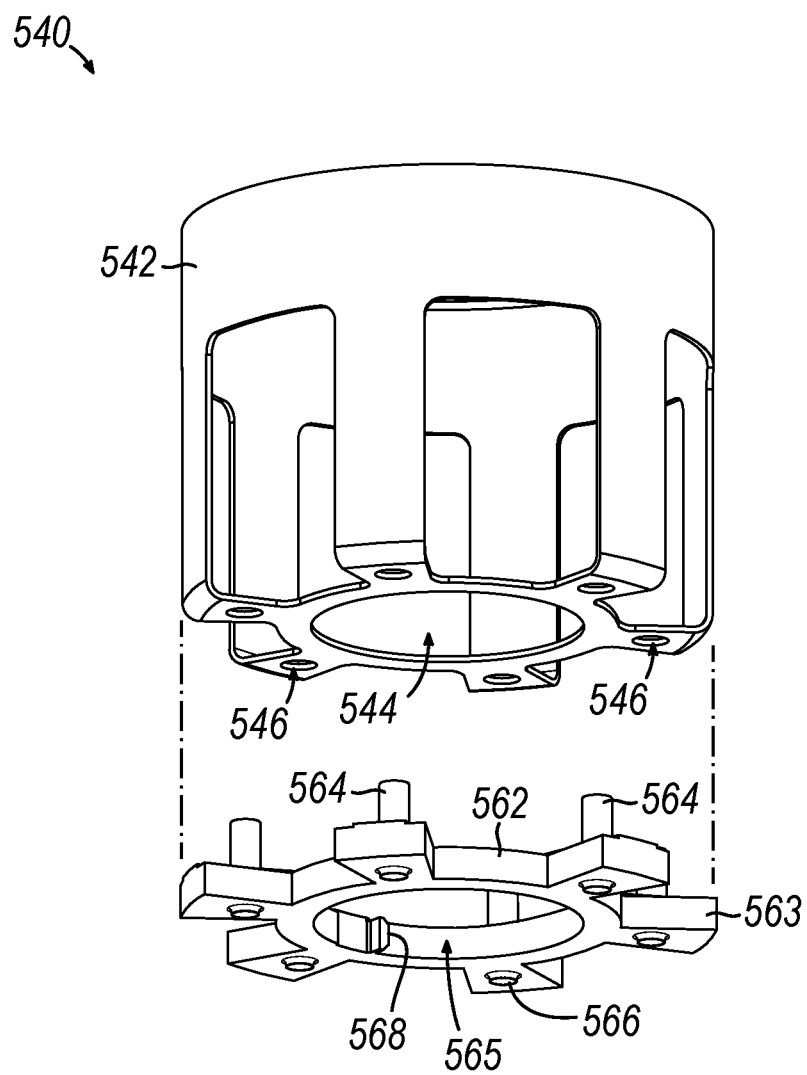
FIG. 11 depicts an exploded perspective view of a cylindraceous knife member of the stapling head assembly of FIG. 8 and a knife coupling ring of a knife retracting assembly of the stapling head assembly.

Turning to FIG. 11, as mentioned above, cylindraceous knife (540) is substantially similar to cylindraceous knife (340), with differences elaborated herein. Therefore, cylindraceous knife (540) may be actuated distally by stapler driver member (550) in order to sever tissue captured between anvil (400) and deck surface (522) during the firing process. However, rather than coupling with studs (340) that are fixed relative to staple drive remember (350), annular array of openings (546) are dimensioned to receive studs (564) of knife coupling ring (562). Studs (564) of knife coupling ring (562) are dimensioned to fit within a respective opening (546) such that rotation of knife coupling ring (562) drives corresponding rotation of knife (540); while translation of knife coupling ring (562) drives corresponding translation of knife (540). In some instances, knife coupling ring (560) may be integral with knife (540) such that coupling via studs (564) and openings (546) are not necessary. In some instances, other suitable coupling means may be used in order to couple knife coupling ring (560) and knife (540) as would be apparent to one skilled in the art in view of the teachings herein. For example, an adhesive may be used to couple ring (560) with knife (540).

Figure 12:
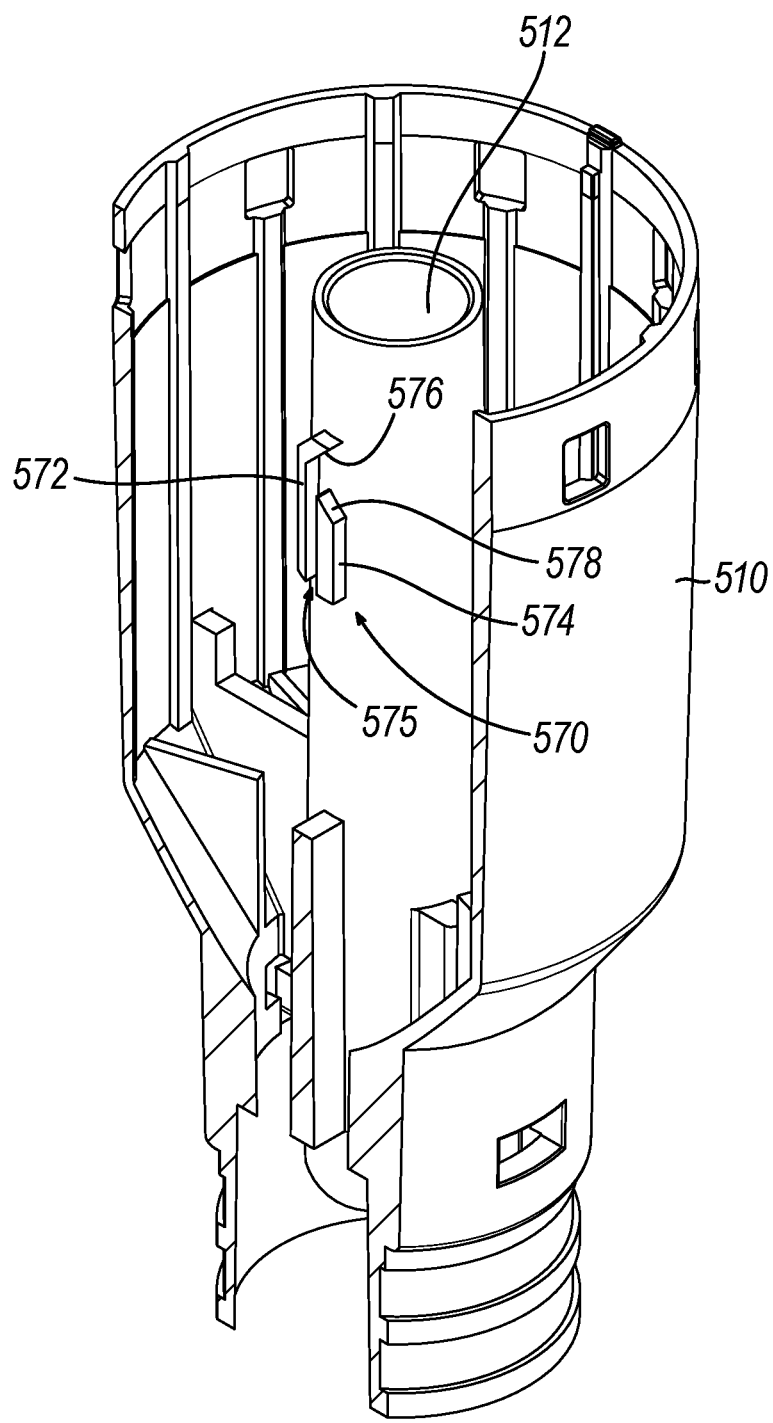
FIG. 12 depicts a sectional view of a tubular body member of the stapling head assembly of FIG. 8, taken along line 12-12 of FIG. 9.

FIGS. 11 and 12 show various components of knife retracting assembly (560). As mentioned above, knife retracting assembly (560) is configured to proximally retract cylindraceous knife member (540) within bore (554) defined by staple driver member (552) after the initial firing of stapling head assembly (500). Knife retracting assembly (560) includes knife coupling ring (560) having a cam feature (568), a complementary cam assembly (570) associated with inner core member (512), and bias element (580) (see FIG. 13A) interposed between knife coupling ring (560) and floor surface (557) of stapler driver member (550). As will be described in greater detail below, during distal advancement of staple driver member (550) to sever and staple tissue, cam feature (568) of knife coupling ring (560) is configured to engage complementary cam assembly (570) of inner core member (512) to thereby rotate knife coupling ring (560) relative to staple driver member (550) and out of engagement with firing ledges (556). With knife coupling ring (560) disengaged from firing ledges (556), biasing element (580) moves knife coupling ring (560) and knife (540) proximally toward floor surface (557) into a retracted position. While knife (540) is in the retracted position, staple driver member (550) may be actuated a second time such that staple drivers (552) extend distally past deck surface (522) while cutting edge (542) of knife (540) remains proximally below deck surface (522).

Figure 13A:
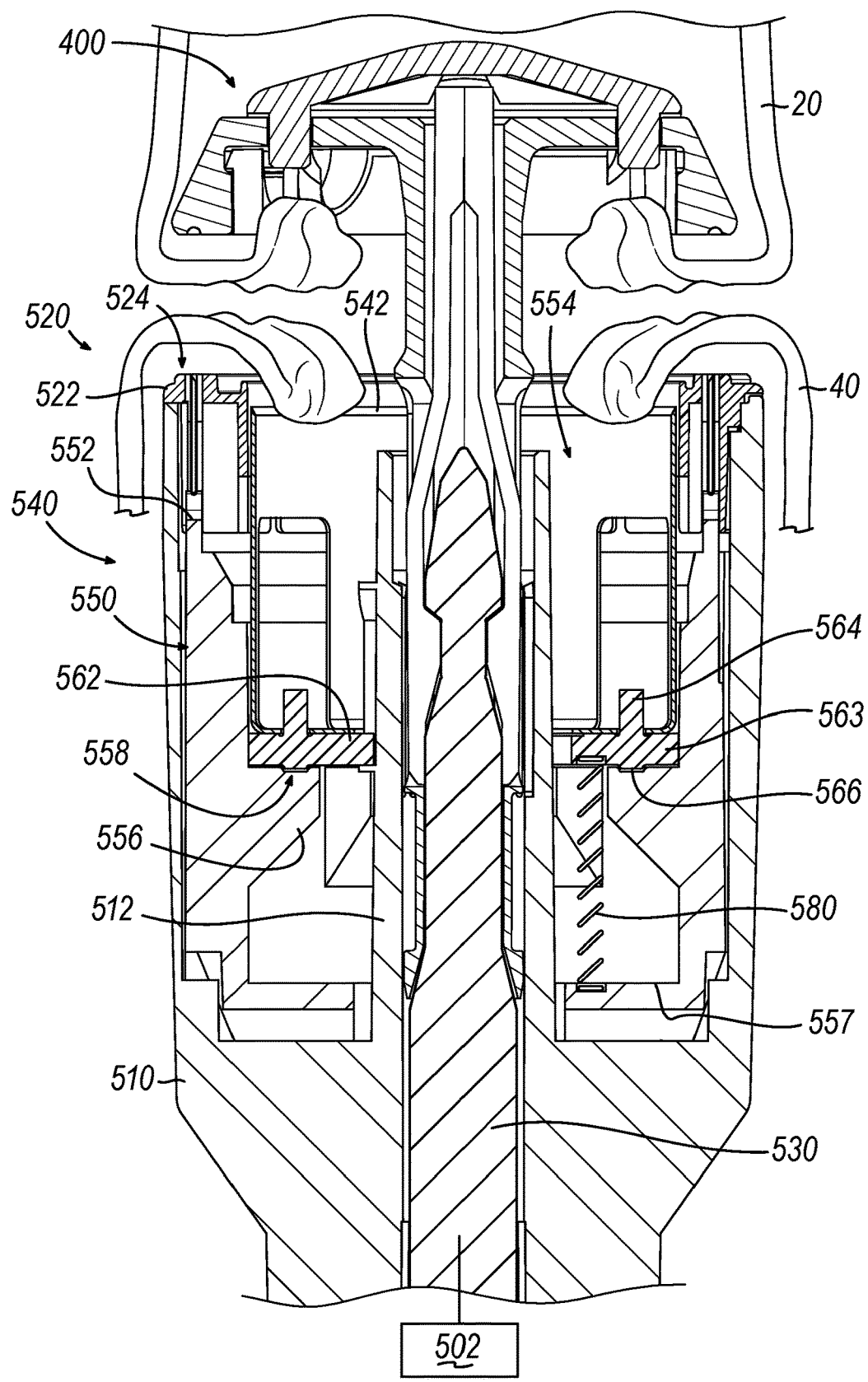
FIG. 13A depicts a cross-sectional side view of the anvil of FIG. 3 positioned within the first section of the digestive tract and the stapling head assembly of FIG. 8 positioned within the second section of the digestive tract, with the anvil secured to the stapling head assembly.

Turning back to FIG. 11, knife coupling ring (560) includes an annular array of ledge engagement bodies (563), each having a respective locating bump (566). As mentioned above, ledge engagement bodies (563) are configured to rest against firing ledges (556) of staple driver member (550). In particular, engagement bodies (563) are configured to rest against firing ledges (556) prior to and during the initial firing of staple driver member (550) such that distal actuation of firing ledges (556) drives distal actuation of engagement bodies (563), knife coupling ring (560), and knife (540). Locating bumps (566) are dimensioned to fit within recessed pockets (558) such that engagement bodies (563) do not unintentionally disassociate with firing ledges (556). As best shown in FIG. 13A, bias element (580), such as a spring, proximally biases knife coupling ring (562) and knife (540). The initial proximal bias provided by bias element (580) may help increase the frictional braking force between recessed pockets (558) and locating bumps (566), which may further help prevent unintentional dissociation between firing ledges (556) and their respective engagement body (563).

Knife coupling ring (560) defines central opening (565) dimensioned to slidably receive inner core member (512). In the current example, cam feature (568) extends radially inward from knife coupling ring (562) toward central opening (565). As will be described in greater detail below, cam feature (568) is configured to engage complementary cam assembly (570) in order to rotate knife coupling ring (560) such that ledge engagement bodies (563) of knife coupling ring (560) no longer engage firing ledges (556) of staple driver member (550).

Turning to FIG. 12, complementary cam assembly (570) includes a first body (572) having a first cam surface (576), and a second body (574) having a second cam surface (578). First body (572) and second body (574) are fixed relative to inner core member (512). First body (572) and second body (574) extend longitudinally along inner core member (512) and together define a guide channel (575). Guide channel (575) is positioned along inner core member and dimensioned to slidably receive cam feature (568) (see FIG. 11) of knife coupling ring (562). First cam surface (576) extends laterally toward second body (574) from the longitudinal path of guide channel (575). As will be described in greater detail below, during or immediately after the firing process to staple and sever tissue in accordance with the description herein, first cam surface (576) is configured to engage cam feature (568) of knife coupling ring (562) during distal advancement in order to rotate ledge engagement bodies (563) out of engagement with firing ledges (556). As will also be described in greater detail below, second cam surface (578) may be configured to engage cam feature (568) during proximal retraction of knife coupling ring (562) toward floor surface (557) of staple driver member (557).

FIGS. 13A-14D show an exemplary use of anvil (400) and staple head assembly (500) in order to staple and sever tissue in accordance with the description herein; while also retracting knife member (540) after severing tissue such that staple drivers (552) may be actuated a second time distally past deck surface (522) in order to push tissue off deck surface (522). As shown in FIG. 13A, anvil (400) may be initially coupled with trocar (530) while anvil (400) and staple head assembly (500) are disposed within their respective lumens (20, 40). Next, anvil (400) may be actuated proximally toward deck surface (522) in order to define a suitable gap distance (d) as shown in FIG. 13B. At the moment shown in FIG. 13B, staple driver number (550) is in the pre-fired position.

In the current example, staple head assembly (500) includes a displacement sensor assembly (502) in communication with motor activation module (180). Displacement sensor assembly (502) may be configured to measure the longitudinal location of trocar (530) relative to staple deck member (520) and generate a signal indicative of the longitudinal location of trocar (400). Therefore, the measurement and signal generated by displacement sensor assembly (502) may be indicative of the gap distance (d) formed by deck surface (522) and anvil (400). As will be described in greater detail below, motor activation module (180) may be configured to reactive motor (160) in response to a signal received by displacement sensor assembly (502) in order to actuate staple drivers (552) distally past deck surface (522) a second time to push tissue off deck surface (522).

Figure 13B:
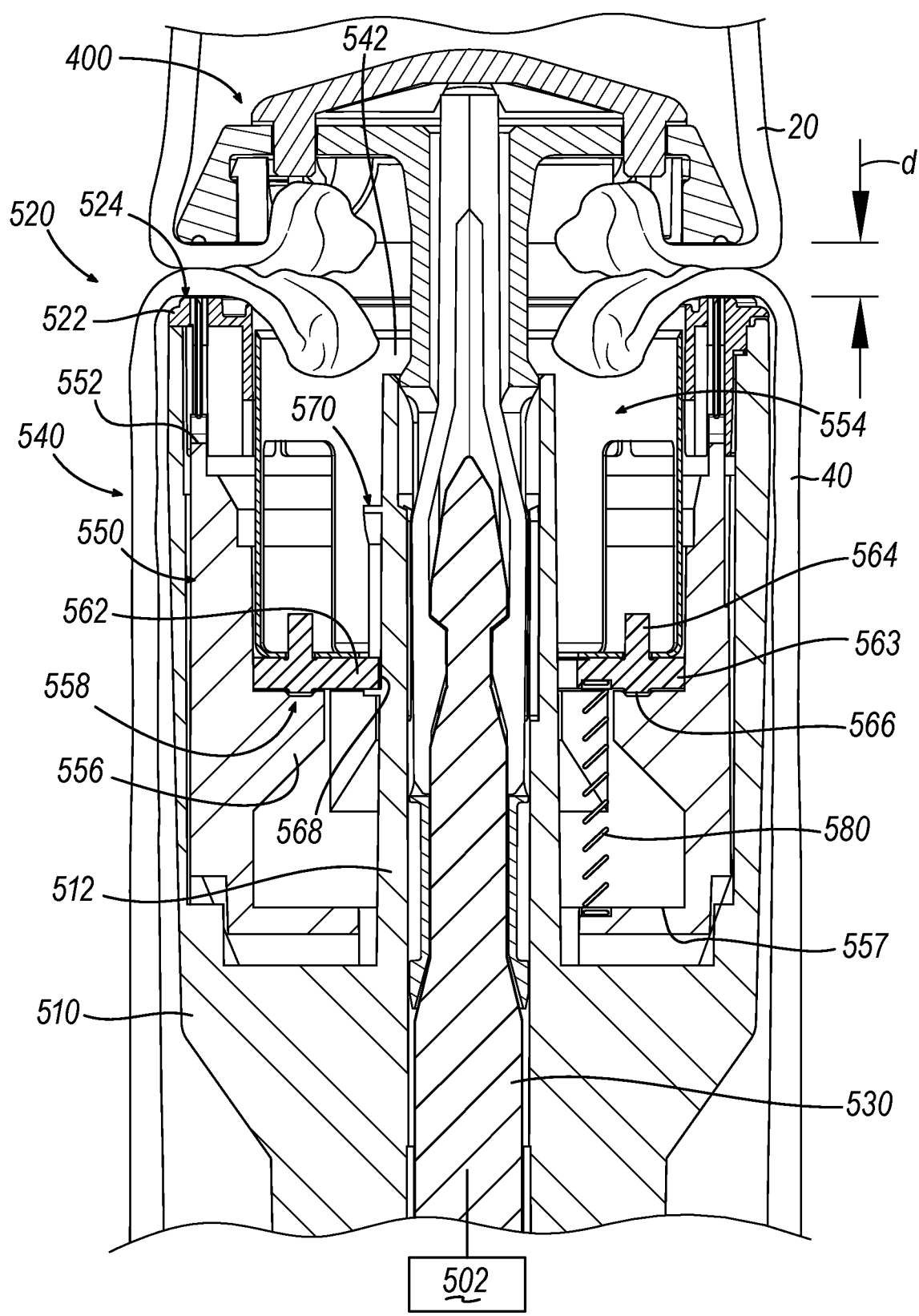
FIG. 13B depicts a cross-sectional side view of the anvil of FIG. 3 positioned within the first section of the digestive tract and the stapling head assembly of FIG. 8 positioned within the second section of the digestive tract, with the anvil retracted toward the stapling head assembly to thereby clamp tissue between the anvil and the stapling head assembly.
Figure 14A:
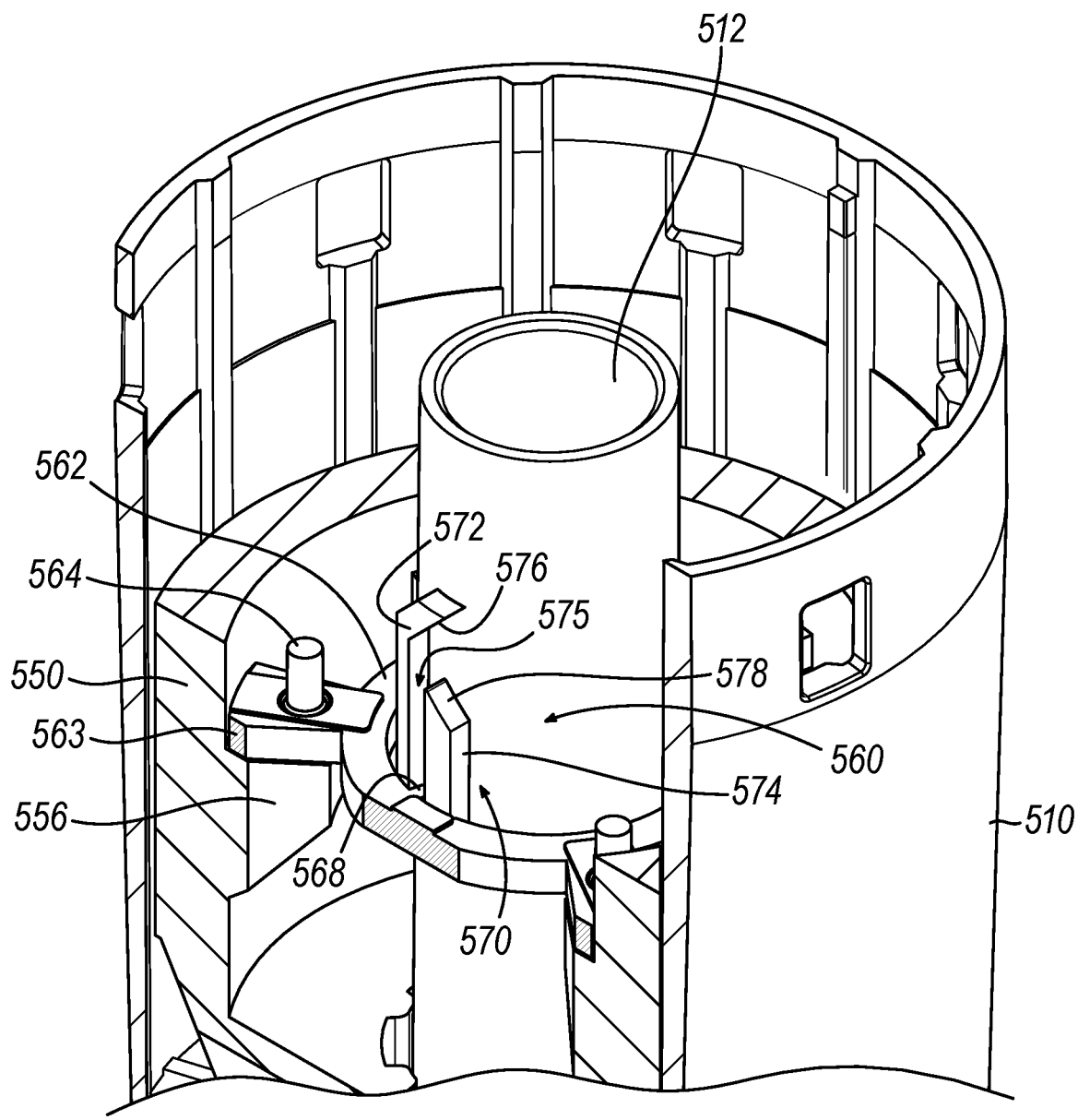
FIG. 14A depicts a sectional view of the stapling head assembly of FIG. 8, taken along line 14-14 of FIG. 8, with certain components omitted for purposes of clarity, with the staple driver member of FIG. 10 and the cylindraceous knife member of FIG. 11 in the position shown in FIG. 13B.

FIG. 14A shows the position of staple driver member (550) relative to knife retracting assembly (560) as also shown in FIG. 13B, with components omitted for purposes of clarity. As shown in FIG. 14A, cam feature (568) of knife coupling ring (562) is located at a proximal portion of guide channel (575), while ledge engagement bodies (563) are suitably coupled with a respective firing ledge (556).

Figure 13C:
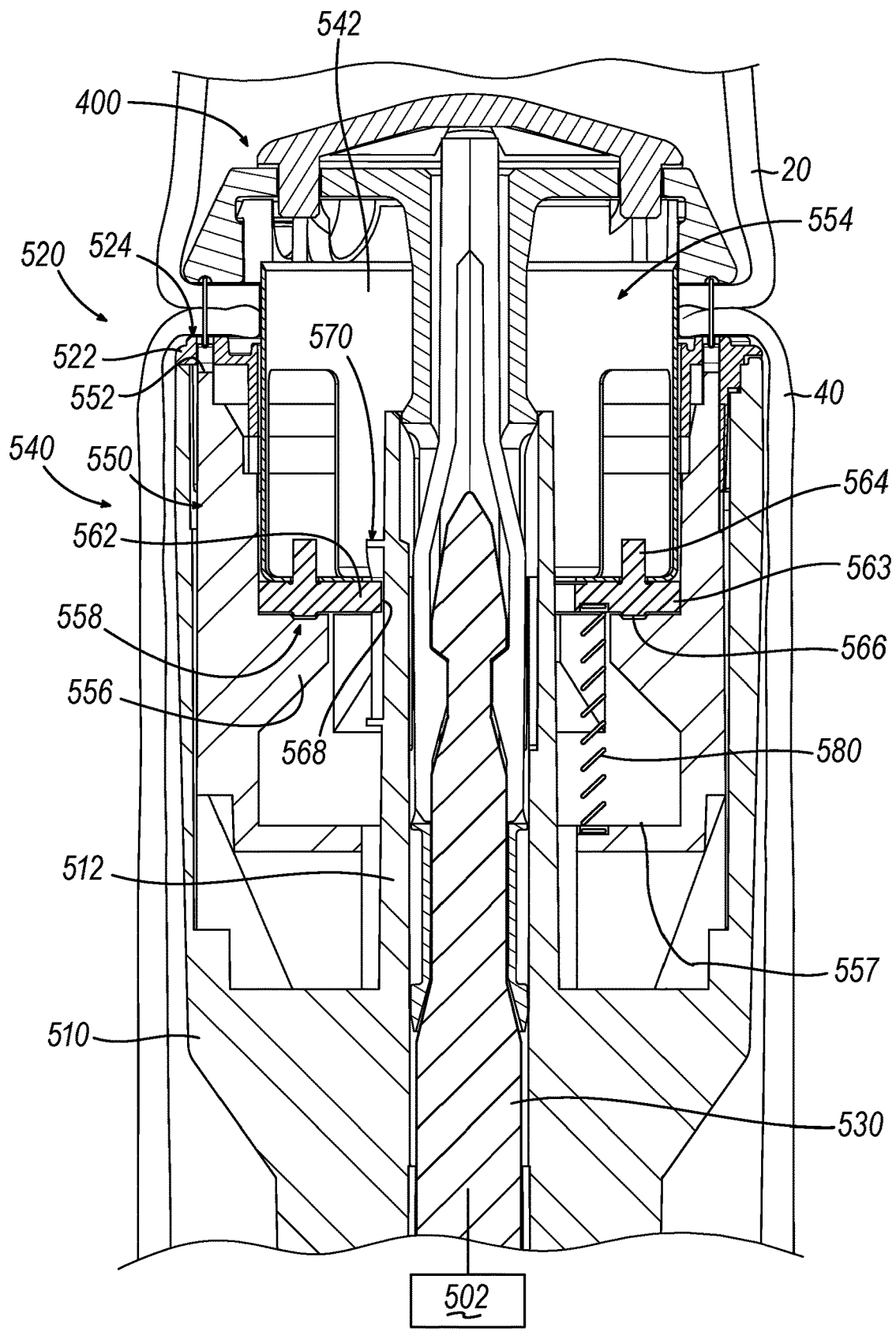
FIG. 13C depicts a cross-sectional side view of the anvil of FIG. 3 positioned within the first section of the digestive tract and the stapling head assembly of FIG. 8 positioned within the second section of the digestive tract, with the stapling head assembly actuated to sever and staple the clamped tissue and thereby joining the first and second sections of the digestive tract.
Figure 14B:
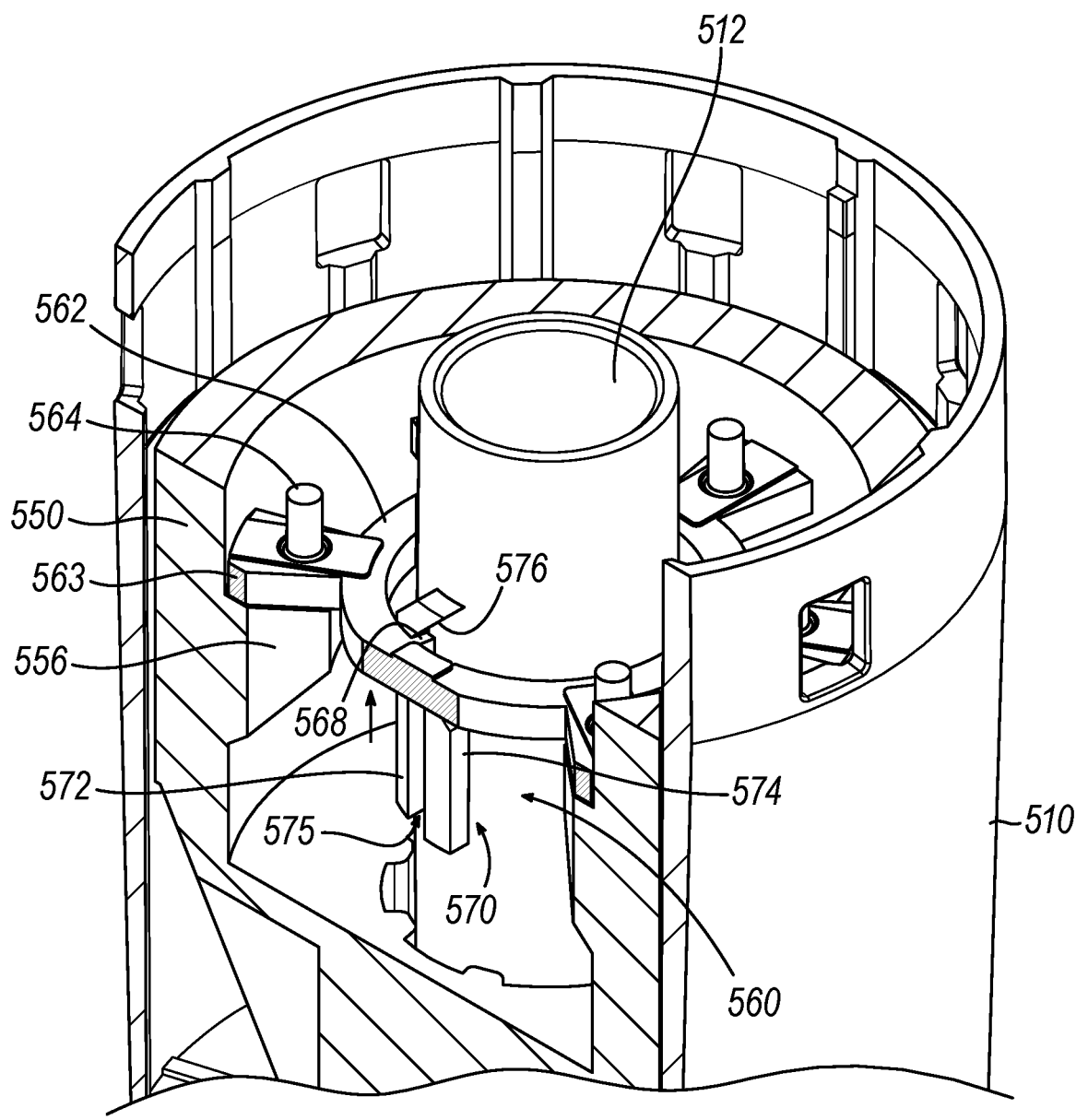
FIG. 14B depicts a sectional view of the stapling head assembly of FIG. 8, taken along line 14-14 of FIG. 8, with certain components omitted for purposes of clarity, with the staple driver member of FIG. 10 and the cylindraceous knife member of FIG. 11 in the position shown in FIG. 13C.

With anvil (400) and deck (522) defining a suitable gap distance (d), the operator may activate the firing process in accordance with the description herein. Therefore, the operator may press firing trigger (150) such that motor (160) drives staple driver member (550) and knife member (540) distally, as shown in FIG. 13C. In the position shown in FIG. 13C, knife member (540) may have suitably severed tissue while staple driver (552) may have suitably fired staples against anvil (400) to staple tissue lumens (20, 40) together, thereby forming an end-to-end anastomosis. FIG. 14B shows the position of staple driver member (550) in the fired position as also shown in FIG. 13C. FIG. 14B shows cam feature (568) of knife coupling ring (562) located at a distal position of guide channel (575), prior to engaging cam surface (576). Therefore, ledge engagement bodies (563) are still suitably coupled with a respective firing ledge (556).

Figure 13D:
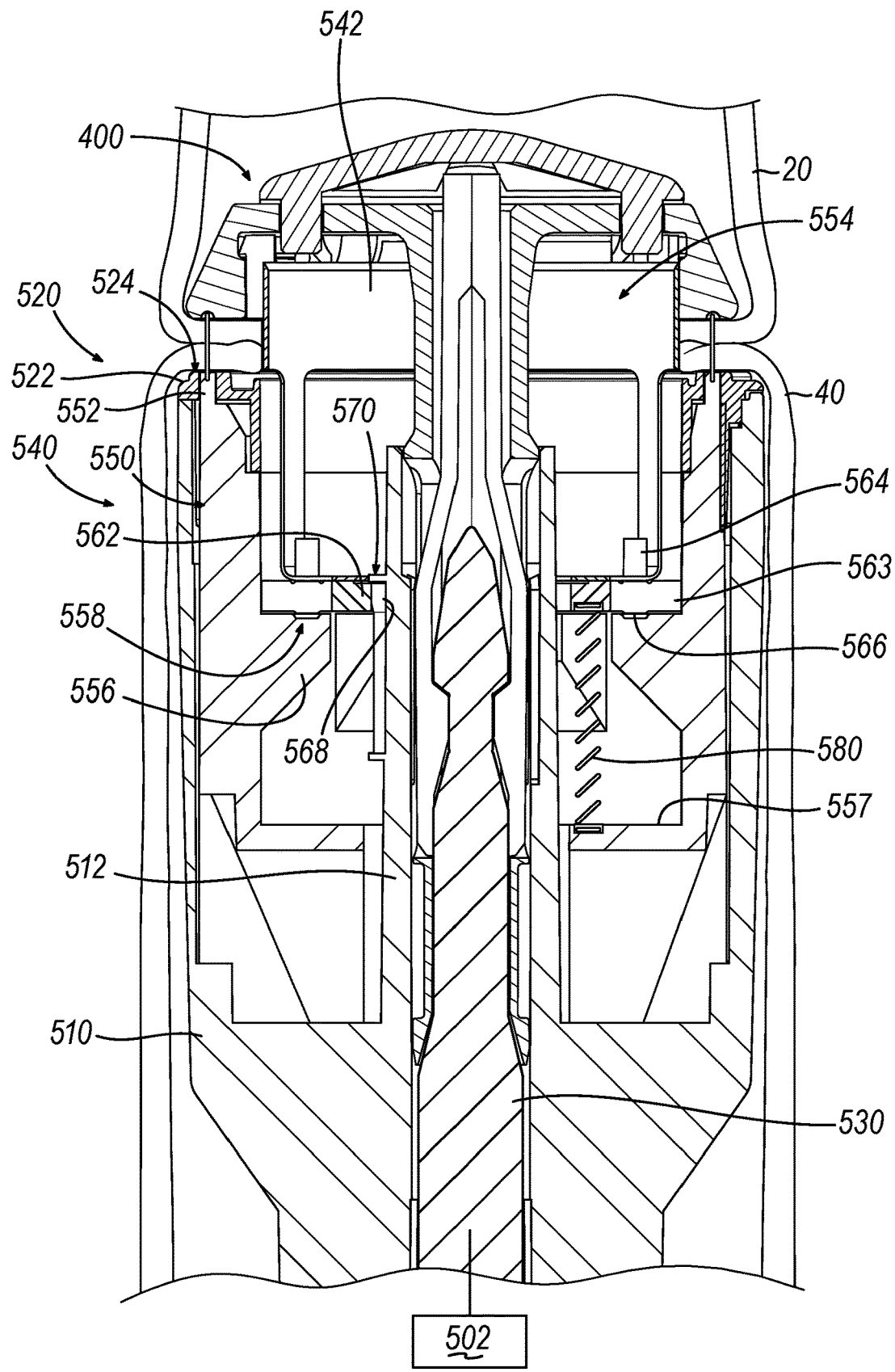
FIG. 13D depicts a cross-sectional side view of the anvil of FIG. 3 positioned within the first section of the digestive tract and the stapling head assembly of FIG. 8 positioned within the second section of the digestive tract, with a knife retracting assembly of the stapling head assembly initially decoupling the cylindraceous knife of FIG. 11 with a plurality of firing ledges of the staple driver member of FIG. 10.
Figure 13E:
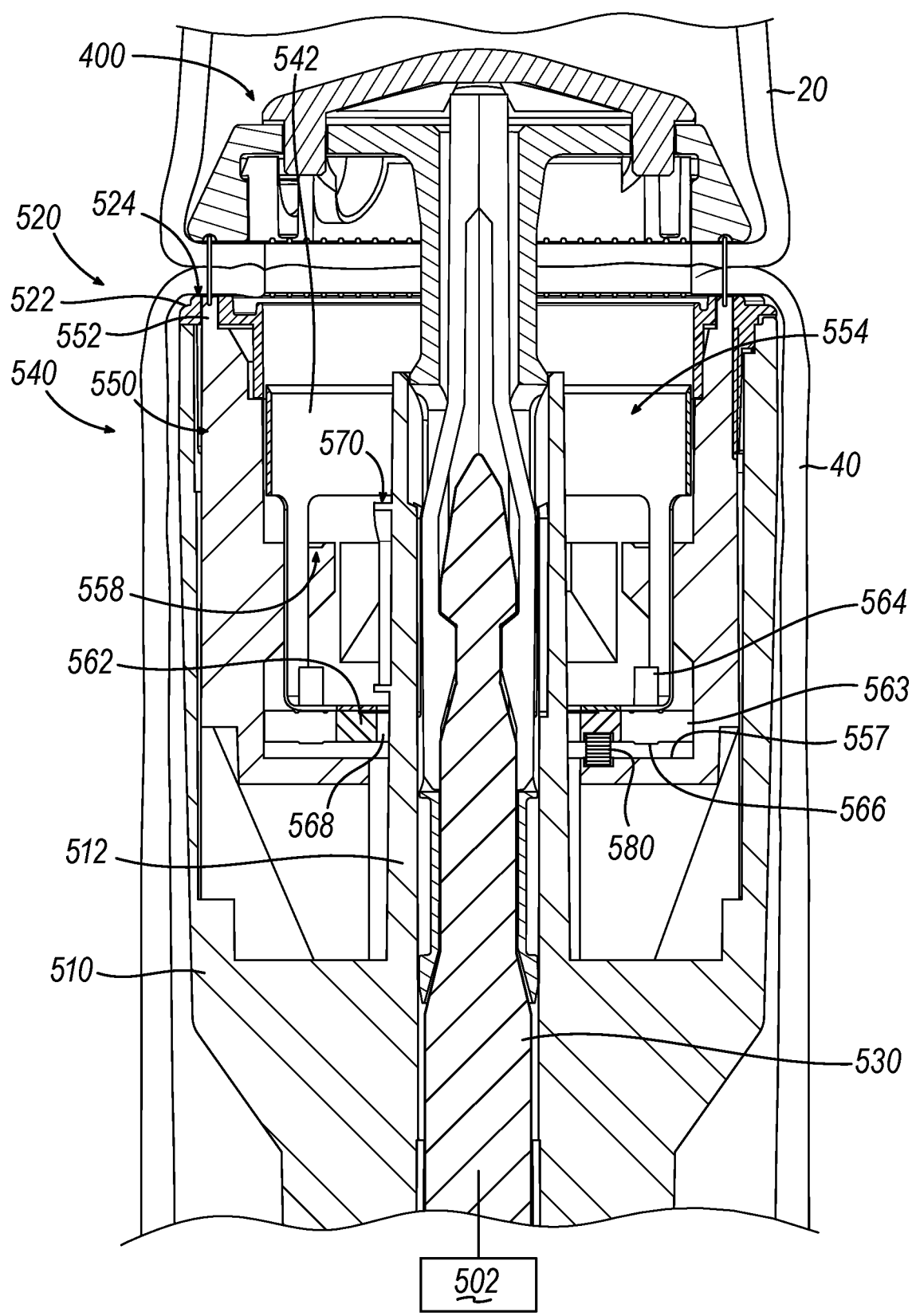
FIG. 13E depicts a cross-sectional side view of the anvil of FIG. 3 positioned within the first section of the digestive tract and the stapling head assembly of FIG. 8 positioned within the second section of the digestive tract, with the cylindraceous knife of FIG. 11 decoupled with a plurality of firing ledges of the staple driver member of FIG. 10 and the stapler driver member in an advanced position.
Figure 14C:
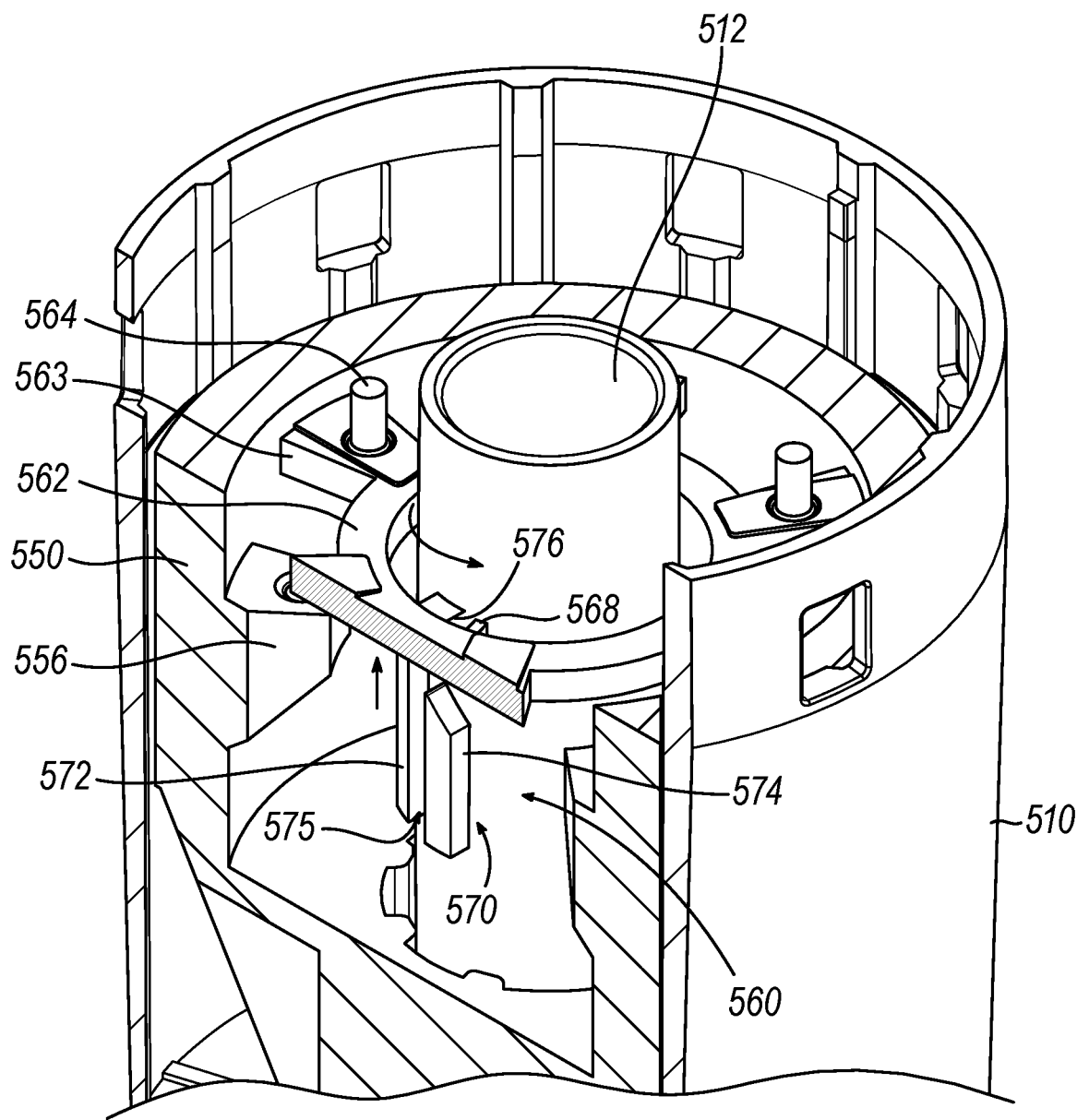
FIG. 14C depicts a sectional view of the stapling head assembly of FIG. 8, taken along line 14-14 of FIG. 8, with certain components omitted for purposes of clarity, with the staple driver member of FIG. 10 and the cylindraceous knife member of FIG. 11 in the position shown in FIG. 13D.
Figure 14D:
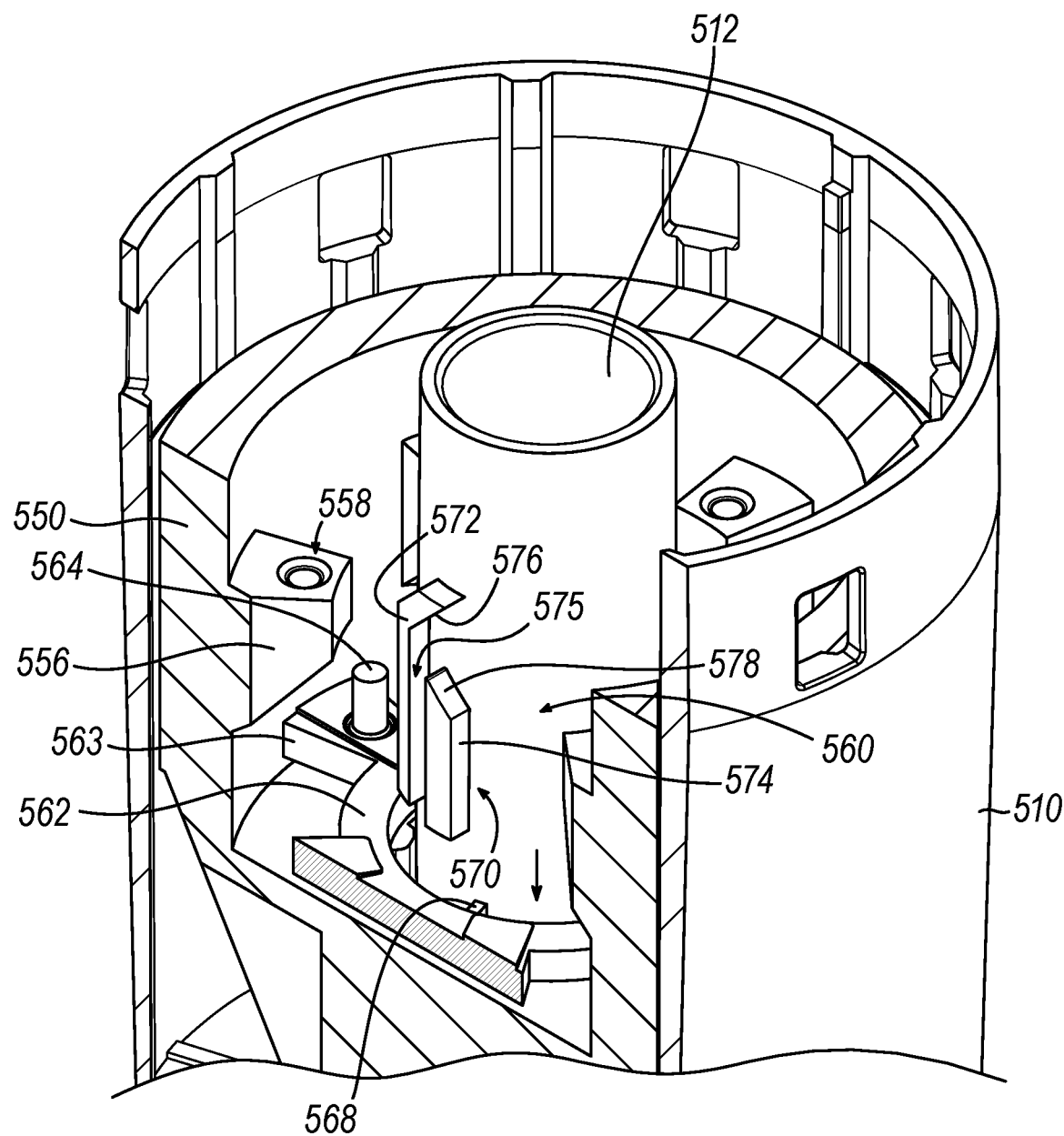
FIG. 14D depicts a sectional view of the stapling head assembly of FIG. 8, taken along line 14-14 of FIG. 8, with certain components omitted for purposes of clarity, with the staple driver member of FIG. 10 and the cylindraceous knife member of FIG. 11 in the position shown in FIG. 13E.

Next, as shown in FIGS. 13D and 14C, motor (16) may actuate staple driver member (550) further in the distal direction such that cam feature (568) abuts against first cam surface (576). As shown in FIG. 14C, interaction between cam feature (568) and cam surface (576) drives rotation of ledge engagement bodies (563) out of engagement with firing ledges (557). As mentioned above, bias element (580) biases knife coupling ring (562) and knife member (540) in the proximal direction. As seen between FIGS. 13D-13E and FIGS. 14C-14D, with ledge engagement bodies (563) and firing ledges (557) disengaged with each other, bias element (580) actuates knife member (540) toward floor surface (577) of stapler driver member (550) into a retracted position. In some instances, cam feature (568) may engage second cam surface (578) in order to ensure cam feature (568) does not accidentally re-enter channel (575). It should be understood that with knife member (540) in the retracted position, sharp circular cutting edge (542) is retracted proximally within bore (554) such that cutting edge (542) may not be actuated distally past deck surface (522) a second time.

Figure 13F:
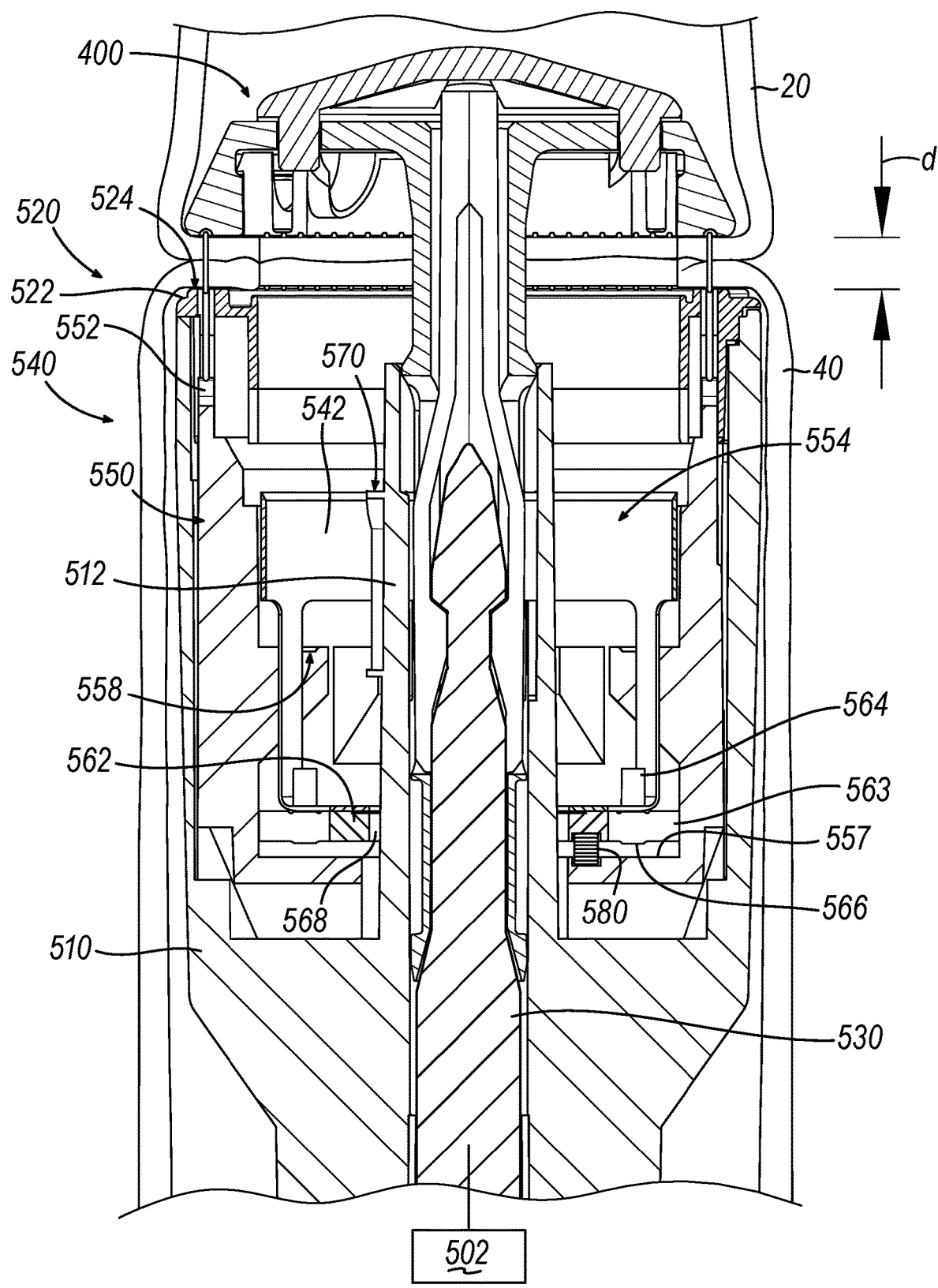
FIG. 13F depicts a cross-sectional side view of the anvil of FIG. 3 positioned within the first section of the digestive tract and the stapling head assembly of FIG. 8 positioned within the second section of the digestive tract, with the cylindraceous knife of FIG. 11 decoupled with a plurality of firing ledges of the staple driver member of FIG. 10 and the stapler driver member in a retracted position.
Figure 13G:
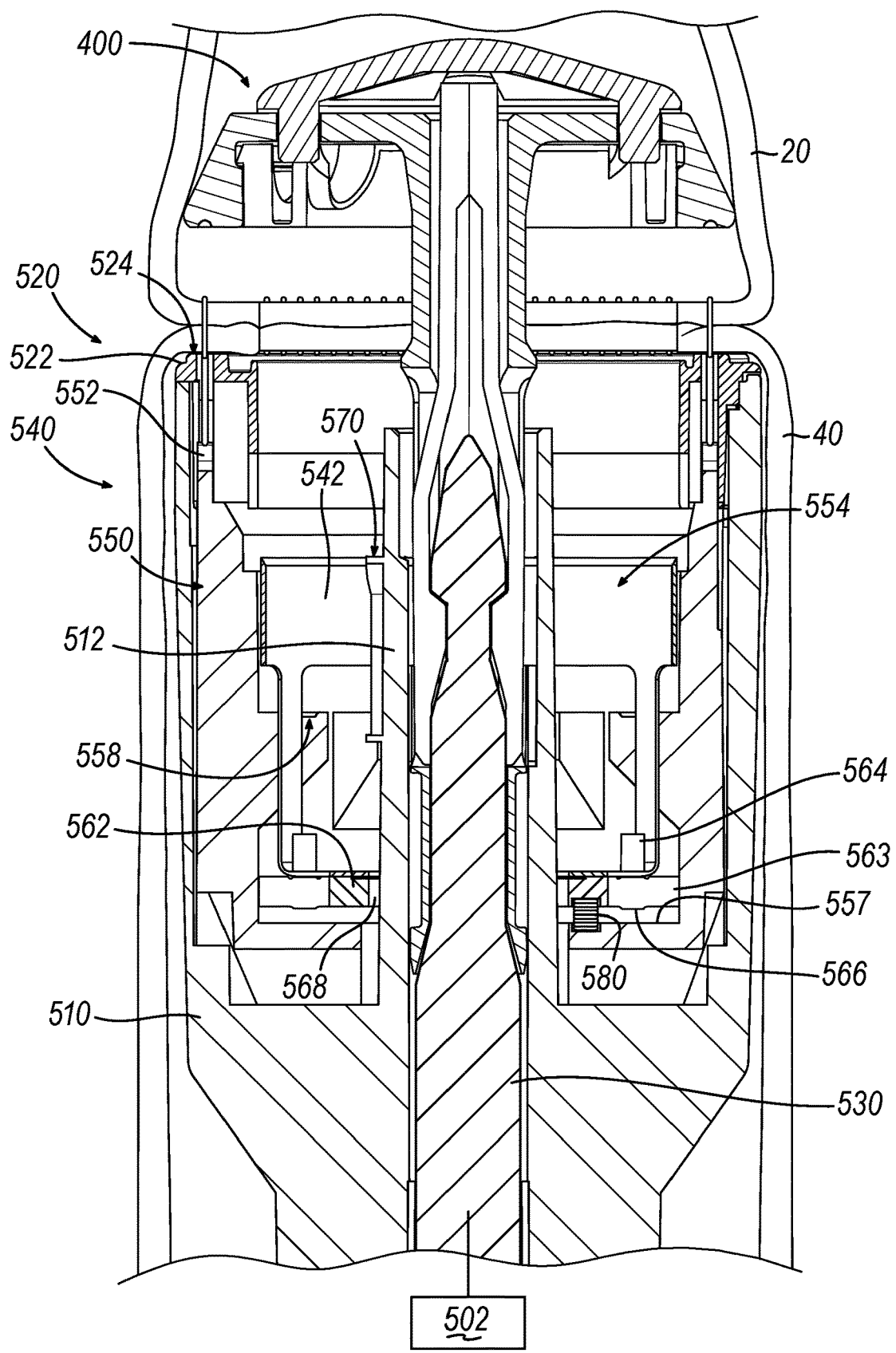
FIG. 13G depicts a cross-sectional side view of the anvil of FIG. 3 positioned within the first section of the digestive tract and the stapling head assembly of FIG. 8 positioned within the second section of the digestive tract, with an end-to-end anastomosis formed and the anvil actuated distally from the stapling head assembly to release the previously clamped tissue between the anvil and the stapling head assembly.

Next, as shown in FIG. 13F, motor (160) may actuate staple driver member (550) proximally back into the pre-fired position such that staple drivers (552) are located proximal relative to deck surface (522). It should be understood, that at the moment shown in FIG. 13F, anatomical structurers (20, 40) may be stapled and severed to form an end-to-end anastomosis. However, the recently severed and stapled tissue of anatomical structure (20, 40) are still being grasped by anvil (400) and deck member (520). Therefore, an operator may distally actuate anvil (400) in accordance with the description herein in order to release grasped tissue, as shown in FIG. 13G.

Figure 13H:
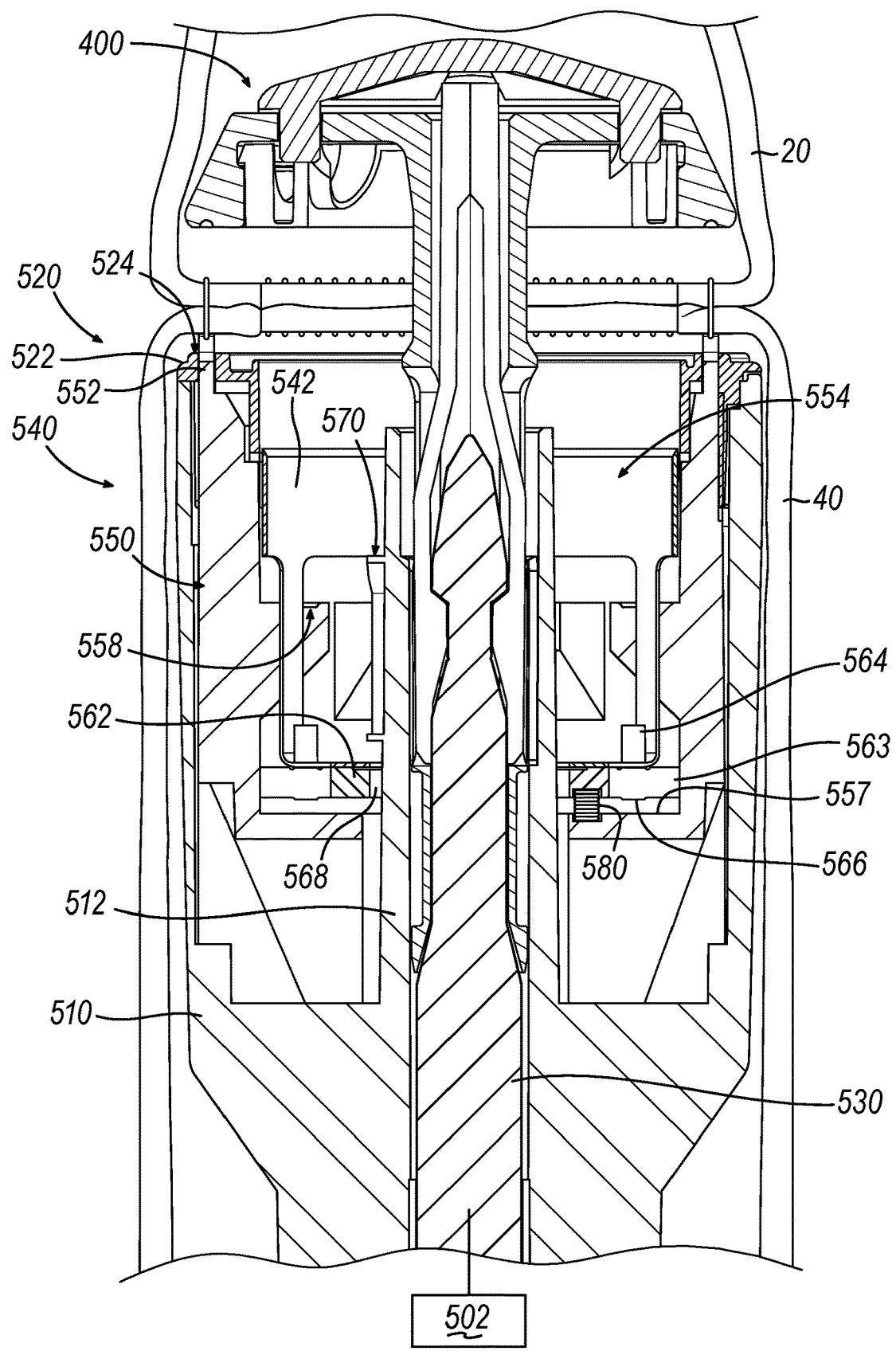
FIG. 13H depicts a cross-sectional side view of the anvil of FIG. 3 positioned within the first section of the digestive tract and the stapling head assembly of FIG. 8 positioned within the second section of the digestive tract, with the staple driver member of FIG. 10 actuated distally a second time to push tissue off an annular deck member of the stapling head assembly.

However, as mentioned above, in some instances, tissue may be undesirably stuck to deck surface (522) such that it may be desirable to push tissue distally off deck surface (522). As also mentioned above, displacement sensor assembly (502) may measure or otherwise detect the longitudinal location of trocar (530), which may be indicative of gap distance (d), and communicate a signal indicative of that longitudinal location to motor activation module (180). Once gap distance (d) is sufficiently large enough to release tissue as determined by motor activation module (180) relative to a predetermined gap distance (d), for example as shown in FIG. 13G, motor activation module (180) may respond to the signal received from displacement sensor assembly (502) by activating motor (160) to distally actuate staple drivers (552) past deck surface (522) a second time, as shown in FIG. 13H, and then proximally actuate staple drivers (552) toward the pre-fired position. Therefore, displacement sensor assembly (502) may be configured to enable and/or provide for the second actuation of staple drivers (522) in response to anvil (400) releasing tissue after the stapling and severing of tissue in accordance with the description herein.

It should be understood that while staple drivers (552) are actuated past deck surface (522) a second time, knife member (540) may remain in the retracted position which is proximal to deck surface (522). Therefore, knife member (540) may be sheathed, contained within bore (554) of staple driver member (550) such that staple drivers (552) may push tissue off deck surface (522) while inhibiting knife member (540) from accidentally severing or otherwise damaging tissue. Therefore, knife retracting assembly (560) may be operative to utilize staple driver member (550) as an anastomosis release feature after the initial stapling and severing of tissue in accordance with the description herein.

Figure 13I:
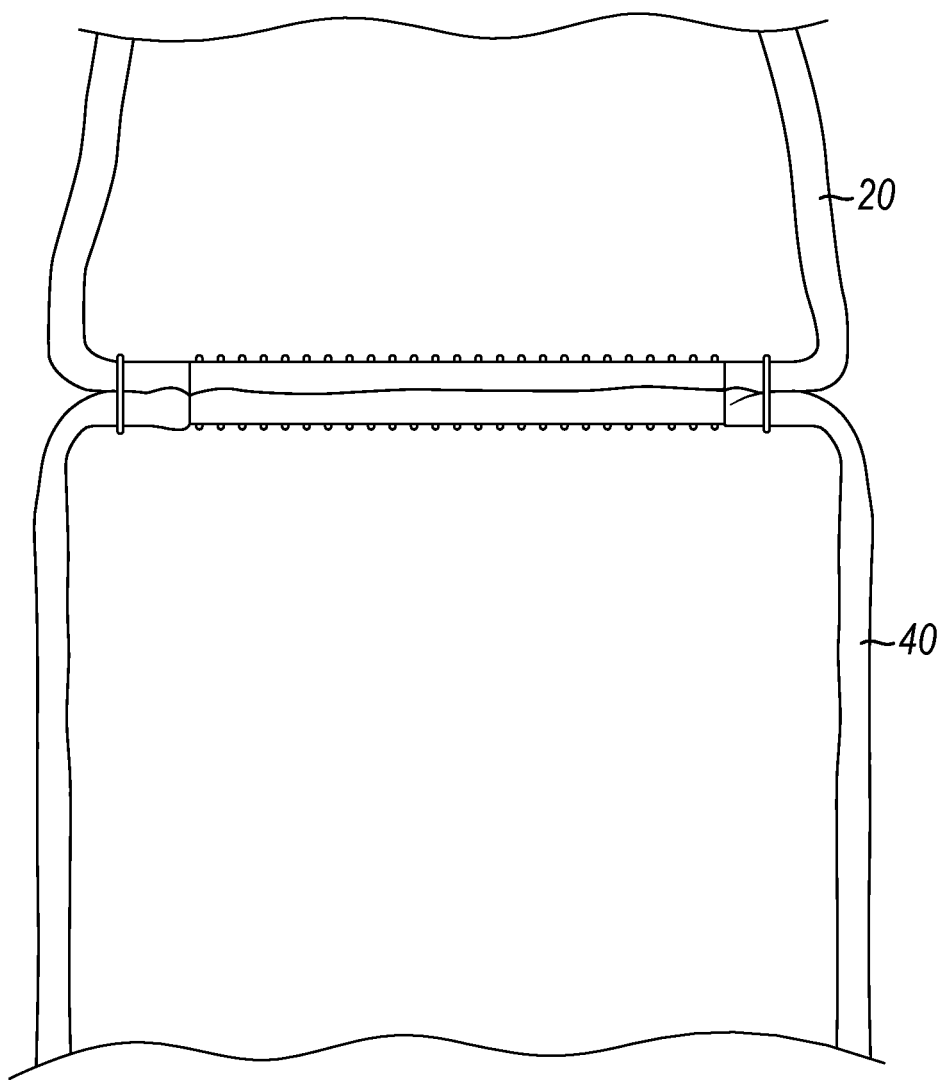
FIG. 13I depicts a cross-sectional side view of the first and second sections of the digestive tract of FIG. 13A joined together at an end-to-end anastomosis formed with the anvil of FIG. 3 and the stapling head assembly of FIG. 8.

With tissue successfully pushed off deck surface (522), the operator may remove staple head assembly (500) and anvil (400) from the patient, thereby forming an end-to-end anastomosis as shown in FIG. 13I.

While in the current example, motor (160) is activated in response to a signal from displacement sensor assembly (502) to drive staple driver member (550) a second time and push tissue off deck surface (522), this is merely optional. In some instances, an operator may be required to press firing trigger (150) a second time after releasing tissue in order to activate motor (160) to actuate staple drivers (552) and push tissue off deck surface (522). Any suitable means of activating motor (160) to drive staple driver member (550) to function as an anastomosis release feature may be utilized as would be apparent to one skilled in the art in view of the teachings herein.

While in the current example, bias element (580) (see FIG. 13A) is interposed between knife coupling ring (560) and floor surface (557) of stapler driver member (550), this is merely optional. Bias element (580) may be interposed between knife coupling ring (560) and another suitable structure to ensure knife (540) is proximally retracted after initial firing in accordance with the description herein. For example, bias element (580) may be interposed between staple deck member (520) and knife coupling ring (560).

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument, comprising: (a) an anvil defining a plurality of staple forming pockets; (b) a stapling head assembly comprising (i) a body, (ii) a coupling member configured to actuate relative to the body to thereby actuate the anvil relative to the body, (iii) a deck surface, wherein the anvil and the deck surface are configured to cooperatively grasp tissue, (iv) a staple driver assembly configured to actuate distally and proximally through a first firing stroke to drive a plurality of staples against the staple forming pockets of the anvil, wherein the staple driver assembly is configured to actuate distally and proximally through a second firing stroke such that a portion of the staple driver assembly actuates distally past the deck surface, and (v) a knife member comprising a cutting edge configured to actuate with the staple driver during the first firing stroke to sever tissue, wherein the knife member is configured to remain in a retracted position relative to the staple driver assembly such that the cutting edge remains proximal relative to the deck surface throughout the second firing stroke; and (c) a retracting assembly configured to drive the knife member into the retracted position during the first firing stroke.

Example 2

The surgical stapling instrument of any one or more of the preceding Examples, wherein the retracting assembly comprises a knife coupling ring attached to the knife member and a cam assembly associated with the body, wherein the cam assembly is configured to rotate the knife coupling ring and the knife member during the first firing stroke.

Example 3

The surgical stapling instrument of any one or more of the preceding Examples, wherein the staple driver assembly comprises a firing ledge, wherein the knife coupling ring comprises a ledge engagement body configured to engage the firing ledge during the first firing stroke in order to actuate the cutting edge to sever tissue, wherein the cam assembly is configured to rotate the ledge engagement body off of the firing ledge during the first firing stroke.

Example 4

The surgical stapling instrument of any one or more of the preceding Examples, wherein the knife coupling ring comprises a projection dimensioned to fit within a guide path defined by the cam assembly.

Example 5

The surgical instrument of any one or more of the preceding Examples, wherein the body comprises a tubular outer member and an inner core member, wherein the cam assembly is associated with the inner member.

Example 6

The surgical instrument of any one or more of the preceding Examples, wherein the knife coupling ring defines a central opening, wherein the inner core member is disposed within the central opening of the knife coupling ring.

Example 7

The surgical instrument of any one or more of the preceding Examples, wherein the knife member comprises a cylindrical knife.

Example 8

The surgical instrument of any one or more of the preceding Examples, further comprising a motor configured to drive the staple driver assembly through the first stroke and the second stroke.

Example 9

The surgical instrument of any one or more of the preceding Examples, further comprising a displacement sensor configured to measure the longitudinal location of the coupling member relative to the body.

Example 10

The surgical instrument of any one or more of the preceding Examples, wherein the motor is configured to initiate the second stroke based on a measurement from the displacement sensor.

Example 11

The surgical instrument of any one or more of the preceding Examples, wherein the knife member is biased toward the retracted position via a biasing element.

Example 12

The surgical instrument of any one or more of the preceding Examples, wherein the biasing element comprises a spring.

Example 13

The surgical instrument of any one or more of the preceding Examples, wherein the spring is interposed between a floor surface of the staple driver assembly and the knife member.

Example 14

The surgical instrument of any one or more of the preceding Examples, further comprising a handle assembly.

Example 15

The surgical instrument of any one or more of the preceding Examples, further comprising a rotary knob associated with the handle assembly, wherein the rotary knob is configured to drive actuation of the coupling member relative to the body.

Example 16

A surgical stapling instrument, comprising: (a) an anvil defining a plurality of staple forming pockets; (b) a stapling head assembly comprising: (i) a body, (ii) a coupling member configured to actuate relative to the body to thereby actuate the anvil relative to the body, (iii) a deck surface, wherein the anvil and the deck surface are configured to cooperatively grasp tissue, (iv) a staple driver assembly configured to drive a plurality of staples against the staple forming pockets of the anvil, and (v) a knife member comprising a cutting edge, wherein the knife member is associated with the staple driver assembly, wherein the knife member is configured to actuate relative to the staple driver assembly between a first position and a retracted position; and (c) a retracting assembly configured to actuate the knife member from the first position into the retracted position in response to distal actuation of the staple driver assembly, wherein the cutting edge is configured to extend distally past the deck surface when the knife member is in the first position, wherein the cutting edge is configured to remain proximal to the deck surface when the knife member is in the retracted position.

Example 17

The surgical stapling instrument of any one or more of the preceding Examples, wherein the deck surface comprises an annular shape.

Example 18

The surgical instrument of any one or more of the preceding Examples, wherein the coupling member comprises a trocar.

Example 19

The surgical instrument of any one or more of the preceding Examples, wherein the retracting assembly comprises a spring, where spring is configured to bias the knife member toward the retracted position.

Example 20

A surgical stapling instrument, comprising: (a) an anvil defining a plurality of staple forming pockets; (b) a stapling head assembly comprising: (i) a body, (ii) a coupling member configured to actuate relative to the body to thereby actuate the anvil relative to the body, (iii) a deck surface, wherein the anvil and the deck surface are configured to cooperatively grasp tissue, (iv) a staple driver assembly configured to actuate distally and proximally through a first firing stroke to drive a plurality of staples against the staple forming pockets of the anvil, wherein the staple driver assembly is configured to actuate distally and proximally through a second firing stroke such that a portion of the staple driver assembly actuates distally past the deck surface, and (v) a knife member comprising a cutting edge configured to actuate with the staple driver during the first firing stroke such that the cutting edge extends distally past the deck surface, wherein the knife member is configured to remain in a retracted position relative to the staple driver such that the cutting edge remains proximal relative to the deck surface during the second firing stroke; and (c) a retractable assembly comprising: (i) a biasing element, (ii) a first cam surface associated with the body, and (iii) a second cam surface associated with the knife member, wherein the first cam surface and the second cam surface are configured to drive the knife member out of operable engagement with the staple driver assembly during the first firing stroke such that the biasing element actuates the knife member into the retracted position.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument, comprising:
   (a) an anvil defining a plurality of staple forming pockets;
   (b) a stapling head assembly comprising:
      (i) a body,
      (ii) a coupling member configured to actuate relative to the body to thereby actuate the anvil relative to the body,
      (iii) a deck surface, wherein the anvil and the deck surface are configured to cooperatively grasp tissue,
      (iv) a staple driver assembly configured to actuate distally and proximally through a first firing stroke to drive a plurality of staples against the staple forming pockets of the anvil, wherein the staple driver assembly is configured to actuate distally and proximally through a second firing stroke such that a portion of the staple driver assembly actuates distally past the deck surface, and
      (v) a knife member comprising a cylindrical knife and a cutting edge configured to actuate with the staple driver during the first firing stroke to sever tissue, wherein the knife member is configured to remain in a retracted position relative to the staple driver assembly such that the cutting edge remains proximal relative to the deck surface throughout the second firing stroke; and
   (c) a retracting assembly configured to drive the knife member into the retracted position during the first firing stroke.

2. The surgical stapling instrument of claim 1, wherein the retracting assembly comprises a knife coupling ring attached to the knife member and a cam assembly associated with the body, wherein the cam assembly is configured to rotate the knife coupling ring and the knife member during the first firing stroke.

3. The surgical stapling instrument of claim 2, wherein the staple driver assembly comprises a firing ledge, wherein the knife coupling ring comprises a ledge engagement body configured to engage the firing ledge during the first firing stroke in order to actuate the cutting edge to sever tissue, wherein the cam assembly is configured to rotate the ledge engagement body off of the firing ledge during the first firing stroke.

4. The surgical stapling instrument of claim 3, wherein the knife coupling ring comprises a projection dimensioned to fit within a guide path defined by the cam assembly.

5. The surgical instrument of claim 4, wherein the body comprises a tubular outer member and an inner core member, wherein the cam assembly is associated with the inner member.

6. The surgical instrument of claim 5, wherein the knife coupling ring defines a central opening, wherein the inner core member is disposed within the central opening of the knife coupling ring.

7. The surgical instrument of claim 1, further comprising a motor configured to drive the staple driver assembly through the first stroke and the second stroke.

8. The surgical instrument of claim 7, further comprising a displacement sensor configured to measure the longitudinal location of the coupling member relative to the body.

9. The surgical instrument of claim 8, wherein the motor is configured to initiate the second stroke based on a measurement from the displacement sensor.

10. The surgical instrument of claim 1, wherein the knife member is biased toward the retracted position via a biasing element.

11. The surgical instrument of claim 10, wherein the biasing element comprises a spring.

12. The surgical instrument of claim 11, wherein the spring is interposed between a floor surface of the staple driver assembly and the knife member.

13. The surgical instrument of claim 1, further comprising a handle assembly.

14. The surgical instrument of claim 13, further comprising a rotary knob associated with the handle assembly, wherein the rotary knob is configured to drive actuation of the coupling member relative to the body.

15. A surgical stapling instrument, comprising:
   (a) an anvil defining a plurality of staple forming pockets;
   (b) a stapling head assembly comprising:
      (i) a body,
      (ii) a coupling member configured to actuate relative to the body to thereby actuate the anvil relative to the body,
      (iii) a deck surface, wherein the anvil and the deck surface are configured to cooperatively grasp tissue,
      (iv) a staple driver assembly configured to drive a plurality of staples against the staple forming pockets of the anvil, and
      (v) a knife member comprising a cutting edge, wherein the knife member is associated with the staple driver assembly, wherein the knife member is configured to actuate relative to the staple driver assembly between a first position and a retracted position; and
   (c) a retracting assembly configured to actuate the knife member from the first position into the retracted position in response to distal actuation of the staple driver assembly, wherein the retracting assembly comprises a spring, wherein the spring is configured to bias the knife member toward the retracted position,
   wherein the cutting edge is configured to extend distally past the deck surface when the knife member is in the first position,
   wherein the cutting edge is configured to remain proximal to the deck surface when the knife member is in the retracted position.

16. The surgical stapling instrument of claim 15, wherein the deck surface comprises an annular shape.

17. The surgical instrument of claim 15, wherein the coupling member comprises a trocar.

18. A surgical stapling instrument, comprising:
   (a) an anvil defining a plurality of staple forming pockets;
   (b) a stapling head assembly comprising:
      (i) a body,
      (ii) a coupling member configured to actuate relative to the body to thereby actuate the anvil relative to the body,
      (iii) a deck surface, wherein the anvil and the deck surface are configured to cooperatively grasp tissue,
      (iv) a staple driver assembly configured to actuate distally and proximally through a first firing stroke to drive a plurality of staples against the staple forming pockets of the anvil, wherein the staple driver assembly is configured to actuate distally and proximally through a second firing stroke such that a portion of the staple driver assembly actuates distally past the deck surface, and (v) a knife member comprising a cutting edge configured to actuate with the staple driver during the first firing stroke such that the cutting edge extends distally past the deck surface, wherein the knife member is configured to remain in a retracted position relative to the staple driver such that the cutting edge remains proximal relative to the deck surface during the second firing stroke; and (c) a retractable assembly comprising:
  (i) a biasing element,
  (ii) a first cam surface associated with the body, and
  (iii) a second cam surface associated with the knife member, wherein the first cam surface and the second cam surface are configured to drive the knife member out of operable engagement with the staple driver assembly during the first firing stroke such that the biasing element actuates the knife member into the retracted position.

* * * * *